United States Patent
Karin et al.

(10) Patent No.: US 10,975,122 B2
(45) Date of Patent: Apr. 13, 2021

(54) EPITOPE AS A TARGET FOR THERAPY OF INFLAMMATORY AUTOIMMUNE DISEASES AND GRAFT REJECTION

(71) Applicant: Technion Research & Development Foundation Limited, Haifa (IL)

(72) Inventors: Nathan Karin, Haifa (IL); Gizi Wildbaum, Kiryat Yam (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 324 days.

(21) Appl. No.: 15/529,095

(22) PCT Filed: Nov. 17, 2015

(86) PCT No.: PCT/IL2015/051107
§ 371 (c)(1),
(2) Date: May 24, 2017

(87) PCT Pub. No.: WO2016/084062
PCT Pub. Date: Jun. 2, 2016

(65) Prior Publication Data
US 2017/0304436 A1 Oct. 26, 2017

Related U.S. Application Data

(60) Provisional application No. 62/083,952, filed on Nov. 25, 2014.

(51) Int. Cl.
*C07K 7/06* (2006.01)
*C07K 14/705* (2006.01)
*G01N 33/564* (2006.01)
*C07K 16/28* (2006.01)
*A61P 37/00* (2006.01)
*A61P 29/00* (2006.01)
*A61P 37/06* (2006.01)
*A61K 39/395* (2006.01)
*A61K 38/17* (2006.01)
*A61K 38/00* (2006.01)
*A61K 39/00* (2006.01)
*C07K 14/435* (2006.01)
*C07K 16/00* (2006.01)

(52) U.S. Cl.
CPC .............. *C07K 7/06* (2013.01); *A61K 38/17* (2013.01); *A61K 39/395* (2013.01); *A61P 29/00* (2018.01); *A61P 37/00* (2018.01); *A61P 37/06* (2018.01); *C07K 14/705* (2013.01); *C07K 16/28* (2013.01); *G01N 33/564* (2013.01); *A61K 38/00* (2013.01); *A61K 2039/505* (2013.01); *C07K 14/435* (2013.01); *C07K 16/00* (2013.01); *C07K 2317/33* (2013.01)

(58) Field of Classification Search
CPC ................................ C07K 7/06; C07K 14/705
See application file for complete search history.

(56) References Cited

U.S. PATENT DOCUMENTS

| | | | | |
|---|---|---|---|---|
| 6,312,941 | B1* | 11/2001 | Carter-Su | C07K 14/4718 435/252.3 |
| 9,005,963 | B2* | 4/2015 | Blanchetot | C07K 16/2812 435/326 |
| 2006/0035834 | A1 | 2/2006 | Karin | |
| 2006/0194265 | A1 | 8/2006 | Morris et al. | |

FOREIGN PATENT DOCUMENTS

| | | |
|---|---|---|
| WO | WO 2004/041179 | 5/2004 |
| WO | WO 2011/086001 | 7/2011 |
| WO | WO2014/033266 | 3/2014 |

OTHER PUBLICATIONS

USPTO Publication Site for Issued and Published Sequences (PSIPS), Sequence(s): 982 of 1441 for Document # US20060194265A1, retrieved from http://seqdata.uspto.gov/?pageRequest=docDetail &DocID=US20060194265A1 on Jun. 14, 2019, two pages (Year: 2006).*
Harlow, E. and Lane, D., Antibodies: A Laboratory Manual (1988) Cold Spring Harbor Laboratory Press, Cold Spring Harbor, NY, pp. 23-26 (Year: 1988).*
Lederman et al. "A single amino acid substitution in a common African allele of the CD4 molecule ablates binding of the monoclonal antibody, OKT4" Mol Immunol. Nov. 1991;28(11):1171-81 (Year: 1991).*
Colman et al. "Effects of amino acid sequence changes on antibody-antigen interactions", Research in Immunology, 1994; 145(1): 33-36 (Year: 1994).*
Harlow, E. and Lane, D., Antibodies: A Laboratory Manual (1988) Cold Spring Harbor Laboratory Press, Cold Spring Harbor, NY, pp. 23-26, 37-47, 55-59, 72-74 (Year: 1988).*
Database NCBI [online] Sep. 9, 2004 CLA-1 [*Homosapiens*] GenBank accession No. CAA80277.1 URL: http://www.ncbi.nlm.nih.gov/protein/CAA80277.1 Sep. 9, 2004.
International Search Report for International App. No. PCT/IL2015/051107 dated Jan. 20, 2016.
Extended European Search Report for Application No. 15863095.4 dated Apr. 4, 2018.

\* cited by examiner

*Primary Examiner* — Christine Foster
(74) *Attorney, Agent, or Firm* — Pearl Cohen Zedek Latzer Baratz LLP

(57) ABSTRACT

The present invention relates to a peptide comprising an epitope within the macrophage scavenger receptor B-I, a method of using the same, a nucleic acid encoding the same and an antibody that binds to the epitope.

11 Claims, 19 Drawing Sheets
Specification includes a Sequence Listing.

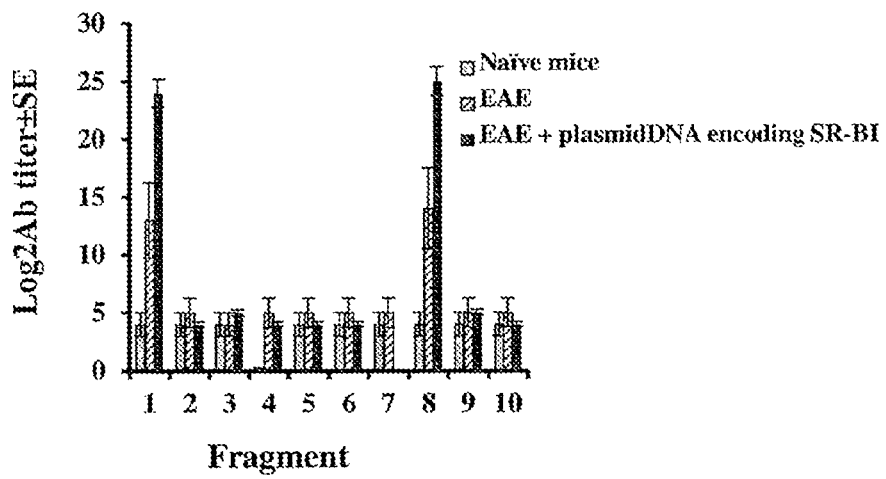
Fig. 1E
CLA-1  IHLVDKWNGLSKVDFWHSDQCNMINGTSGQMWPPFMTPESSI EFYSPEACRSM KLMYKESGVFE
SR-BI  IHLVDKWNGLSEVKYWHSEQCNMINGTAGQMWAPFMTPESSI EFFSPEACRSM KLTYQESRVFE
SR-BI: 273- EFFSPEACRSM -283
CLA-1: 273- EFYSPEACRSM -283
Fig. 1F
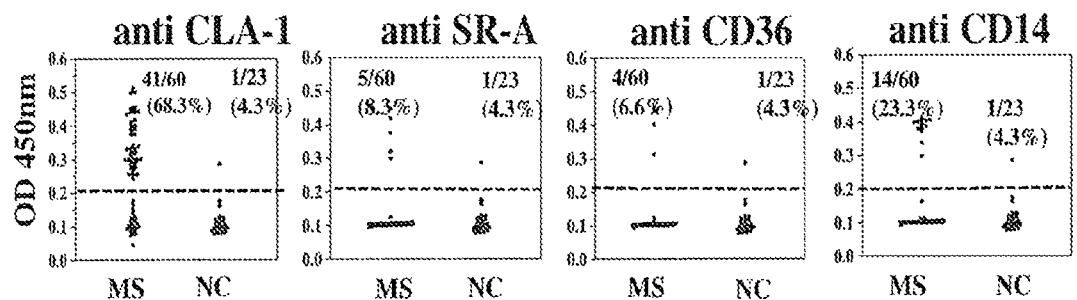
Fig. 2A

*P<0.01

*p<0.001

*p<0.001

EPITOPE AS A TARGET FOR THERAPY OF INFLAMMATORY AUTOIMMUNE DISEASES AND GRAFT REJECTION

CROSS-REFERENCE TO RELATED APPLICATIONS

This application is a National Phase Application of PCT International Application No. PCT/IL2015/051107, International Filing Date Nov. 17, 2015, claiming the benefit of U.S. Provisional Patent Application No. 62/083,952, filed Nov. 24, 2014, which is hereby incorporated by reference.

FIELD OF THE INVENTION

The present invention relates to a peptide comprising an epitope within the macrophage scavenger receptor B-I, a method of using the same, a nucleic acid encoding the same and an antibody that binds to the epitope.

BACKGROUND OF THE INVENTION

Inflammation is a physiological condition characterized in the acute form by the classical signs of pain, heat, redness, swelling and loss of function. Inflammation often accompanies diseases such as Multiple Sclerosis (MS), osteoarthritis, Inflammatory Bowel Disease (IBD) including Crohn's disease and ulcerative colitis, Rheumatoid Arthritis (RA), SLE, type I diabetes (IDDM), atherosclerosis, encephalomyelitis, Alzheimer's disease, stroke, traumatic brain injury, Parkinson's disease, septic shock and others. In most cases, there is no effective cure for inflammation associated with such diseases and existing treatments are palliative and largely fail to control the underlying causes of tissue degradation.

Scavenger receptors (SRs) are cell surface proteins, which are typically found on macrophages and bind various types of chemically modified lipoproteins, such as low-density lipoprotein (LDL). This family of trans-membrane receptors, which are highly varied in structure, are involved in receptor-mediated endocytosis, phagocytosis of apoptotic cells and bacteria, as well as cell adhesion. Since the massive receptor-mediated uptake of cholesterol from modified LDL can convert cultured macrophages into cholesteryl ester-filled foam cells, similar to those found in atherosclerotic plaques, it has been postulated that these receptors also function in deposition of LDL cholesterol of macrophages in artery walls during the initial stages of atherosclerotic plaque formation.

SRs are termed as such since they mediate the binding of a remarkably wide variety of polyanionic ligands, e.g., modified proteins, sulfated polysaccharides and certain polynucleotides. This property led to the hypothesis that these receptors form a part of an in innate immune response by serving as pattern recognition receptors that bind a wide variety of pathogen components.

SR-B1 (also referred to as SR-BI or CLA-I) is a macrophage scavenger molecule and a receptor for high-density lipoprotein (HDL) that mediates cholesterol uptake from cells. SR-B1 can also serve as a receptor for non-HDL lipoproteins and appears to play an important role in reverse cholesterol transport. In vivo experiments showed that this receptor is important for HDL metabolism in mice, and for the metabolism of LDL and HDL cholesterol in humans.

PCT Publication No. WO 2004/041179 teaches targeting of scavenger receptor SR-B1 (ClA-I) for the treatment of infection, sepsis and inflammation. This prior art teaches primarily targeting SR-B1 using amphipathic peptides, which compete with the amphipathic helices in apoliprotein ligands of SR-B1. PCT Publication No. WO 2004/041179 does not provide experimental results for treating autoimmune diseases such as IBD and multiple sclerosis by down-regulating activity or expression of SR-B1, nor does it teach the use of oligonucleotide technology (e.g., antisense, siRNA) and DNA vaccination for targeting SR-B1 and treating inflammatory diseases. Moreover, since PCT Publication No. WO 2004/041179 refers to amphipathic peptides, which are similar or derived from a portions of the apoliprotein ligands, these amphipathic peptides may be misleadingly targeted or bind also to other cell components or molecules, which natively interact with apoliprotein ligands, other than SR-B1.

There is thus, a widely recognized need for, and it would be highly advantageous to have, novel highly specific agents and methods using the same for targeting SR-B1 and treating inflammatory and autoimmune diseases.

SUMMARY OF THE INVENTION

Embodiments of the invention are directed to a peptide comprising the amino acid sequence set forth in EFYSPEACRSM (SEQ ID NO: 1) or EFFSPEACRSM (SEQ ID NO: 2) or any functionally related variant thereof.

Further embodiments of the invention are directed to an antibody or antibody binding fragment or a functionally variant thereof, which recognizes or forms a molecular complex with the peptide set forth in SEQ ID NO: 1 or SEQ ID NO: 2 or with a fragment thereof, on the surface of the macrophage scavenger receptor protein. Additional embodiments are directed to an antibody or antibody binding fragment or a functionally variant thereof, which recognizes or forms a molecular complex with the peptide or with a fragment of the peptides disclosed herein.

Embodiments of the invention are directed to a peptide comprising the amino acid sequence set forth in EFYSPEACRSM (SEQ ID NO: 1) or EFFSPEACRSM (SEQ ID NO: 2) or any of the functionally related variant thereof comprising at least the amino acid residues that contribute most of the binding energy for a complex between the peptide and the antibody or antibody binding fragment disclosed herein.

Further embodiments of the invention are directed to a peptide comprising the amino acid sequence set forth in EFYSPEACRSM (SEQ ID NO: 1) or EFFSPEACRSM (SEQ ID NO: 2) or any of the functionally related variant thereof comprising at least the interface amino acid residues of a complex between the peptide and the antibody or antibody binding fragment disclosed herein. Further embodiments of the invention are directed to a peptide having at least 90% homology to such a peptide, as disclosed herein.

Further embodiments of the invention are directed to a functionally equivalent molecule that mimics a functional activity of the peptide disclosed herein and of any of the functionally related variants thereof, wherein the molecule is a peptidomimetic or a stapled peptide or a chemical compound.

Embodiments of the invention are directed to a method for the preparation of an antibody or antibody binding fragment as disclosed herein, wherein the method comprising the step of administering the peptide disclosed herein or a functionally equivalent molecule, as disclosed, to a subject; and eliciting an immune response to the peptide or the functionally equivalent molecule of the peptide.

Additional embodiments are directed to a pharmaceutical composition comprising a therapeutically effective amount of peptide disclosed herein or comprising a functionally equivalent molecule, as disclosed, and a pharmaceutically acceptable carrier or excipient. Further embodiments are directed to a pharmaceutical composition comprising a therapeutically effective amount of antibody or antibody binding fragment, as disclosed herein, and a pharmaceutically acceptable carrier or excipient.

Embodiments of the invention are directed to an isolated polynucleotide encoding a peptide disclosed herein. Further embodiments are directed to an isolated polynucleotide encoding an antibody or antibody binding fragment, as disclosed herein.

Further embodiments of the invention are directed to a plasmid or a vector comprising the isolated polynucleotide, as disclosed herein. Additional embodiments are directed to a pharmaceutical composition comprising a therapeutically effective amount of the polynucleotide disclosed herein and a pharmaceutically acceptable carrier or excipient.

Further embodiments are directed to a method of reducing an inflammatory response in a subject in need thereof, the method comprising providing to a subject in need thereof a therapeutically effective amount of the pharmaceutical composition disclosed herein. Additional embodiments are directed to a method of treating an inflammatory and/or autoimmunity and/or neuroinflammation disease/s in a subject in need, the method comprising providing to the subject in need thereof a therapeutically effective amount of the pharmaceutical composition disclosed herein.

Additional embodiments are directed to a method of preventing graft rejection comprising providing to a subject in need thereof a therapeutically effective amount of the pharmaceutical composition disclosed herein.

Further embodiments are directed to the pharmaceutical compositions disclosed herein for reducing an inflammatory response, for treating an inflammatory and/or autoimmunity and/or neuroinflammation disease, or for preventing graft rejection in a subject in need thereof.

Additional embodiments are directed to a vaccine comprising an effective amount of a peptide or a functionally equivalent molecule disclosed herein and optionally an adjuvant. Further embodiments of the invention are directed to a vaccine comprising an effective amount of polynucleotide as disclosed herein and optionally an adjuvant.

Embodiments of the invention are directed to a method of diagnosing predisposition to, or presence of, an inflammatory and/or autoimmunity and/or neuroinflammation disease in a subject comprising the steps of: contacting a sample from the subject with a peptide disclosed herein or a functionally equivalent molecule disclosed herein, and detecting the level of anti scavenger receptor autoantibodies in the biological sample obtained from the subject, wherein a detection level above a predetermined threshold of the autoantibodies in the biological sample is indicative of the inflammatory and/or autoimmunity and/or neuroinflammation disease in the subject.

Further embodiments are directed to a kit to aid in measuring the level of an antibody that binds to the scavenger receptor B-I (SR-BI/CLA-1), comprising at least one capture molecule, which is the peptide disclosed herein or functionally equivalent molecule of the peptide disclosed herein; and at least one detector molecule, wherein the detector molecule optionally further comprises a detectable label.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1 B presents a graph showing amplification of anti SR-BI antibody title by SR-BI encoding DNA plasmid. Results of sera of six mice are shown as mean Log2Ab titer±SE (triplicates).

FIG. 1 C demonstrates that administration of a DNA plasmid encoding SR-BI during EAE suppresses an ongoing disease. Results are shown as mean EAE score of six mice per group±SE.

FIG. 1 D is a graph showing that autoantibodies to SR-BI generated in DNA vaccinated mice transfer disease resistance.

Results are shown as mean EAE score of six mice per group±SE.

FIG. 1 E provides epitope mapping of autoantibodies to SR-BI generated in EAE mice treated with DNA plasmid encoding SR-BI.

FIG. 1 F provides the comparison between amino acids 231-294 of SR-B1 (SEQ ID NO: 37) and amino acids 231-294 of CLA-1 (SEQ ID NO: 38). SR-BI: 273-EFF-SPEACRSM-283 (SEQ ID NO: 2); CLA-1: 273-EFY-SPEACRSM-283 (SEQ ID NO: 1).

FIG. 2 A demonstrates the development of autoantibodies to CLA-1, SR-A, CD36 and CD14 determined at a single sera dilution of 1:500 by OD readout at 450 nm. The cut-off was determined using ROC curve analysis as specified herein.

FIG. 2 B presents a graph of anti CLA-1 antibodies in MS subjects .vs. patients with viral encephalitis at a single sera dilution of 1:500 by OD readout at 450 nm.

FIG. 2 C presents the development of autoantibodies to CLA-1 in RA patients determined at a single sera dilution of 1:500 by OD readout at 450 nm.

FIG. 2 D presents analyses of anti CLA-1 and anti CD36 antibody titer in sera of MS patients. Results are presented as $\log_2$Ab titer of triplicates±SE.

FIG. 2 E presents the development of autoantibodies to CLA-1 273-283 determinant in MS patients.

FIG. 2 F presents the effect of anti CLA-1 autoantibodies on the production of IL-10 and TNF-α in PMA-induced macrophage-like THP-1 cells. Results are shown as mean±SE of triplicates.

FIG. 2 G presents the effect of anti CLA-1 autoantibodies on the production of IL-10 and TNF-α in freshly isolated human CD4+ T cells undergoing anti CD3&CD28 induced activation. Results are shown as mean±SE of triplicates.

FIG. 3 A presents flow cytometry analysis of the expression of SR-BI on CD11b+ peritoneal macrophages before and after LPS induced activation in C57BL6 GFP reporter mice.

FIG. 3 B presents dose dependent effect of E12mAb on the production of IL-10, TNF-a and IL-12 on peritoneal macrophages activated by LPS. Results are shown as mean cytokine level as determined by ELISA±SE (triplicates).

FIG. 3 C presents dose dependent effect of E12mAb on the production of IL-10, TNF-a and IL-12 on Zymosan. Results are shown as mean cytokine level as determined by ELISA±SE (triplicates).

FIG. 3 D presents flow cytometry analysis for CD206 expression on peritoneal macrophages activated by LPS and then supplemented with E12 mAb or control IgG1.

Figure 3A:
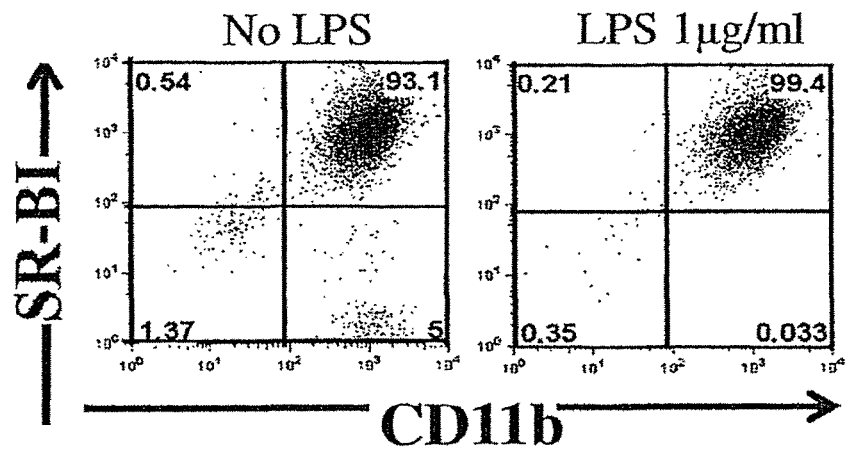
Figure 3B:
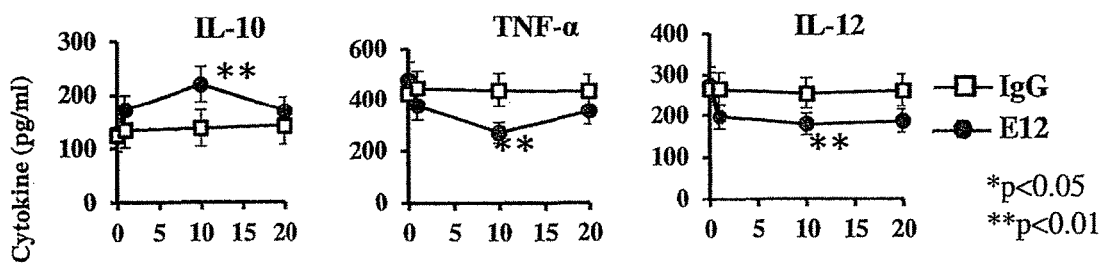
Figure 3C:
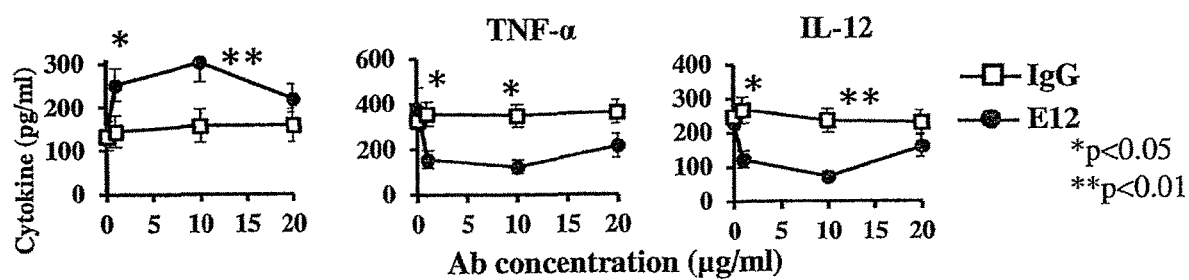
Figure 3D:
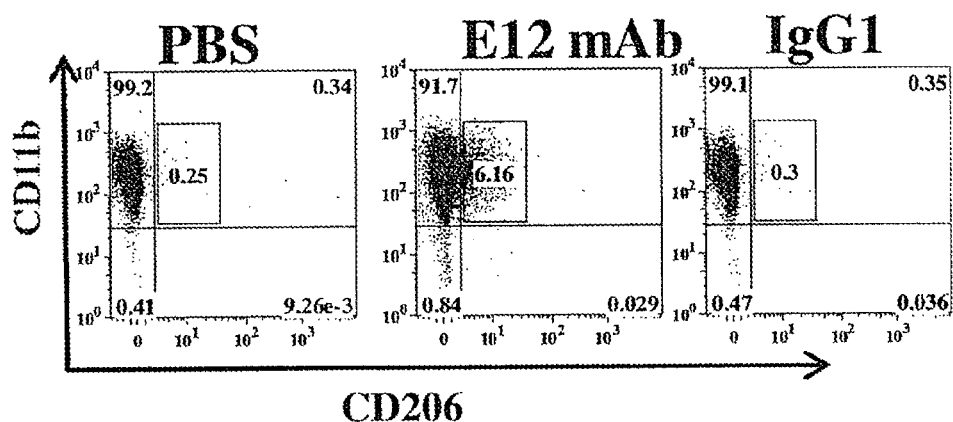

FIG. 3 E presents flow cytometry analysis of IL-10 in CD206+ cells of FIG. 3D.

FIG. 3 F presents the cleavage of E12 mAb into either single F(ab') or F(ab')$_2$ by enzymatic cleavage. Each fragment was then detected for its ability to induce Ca++flux in THP-1 cells.

FIG. 3 G presents the cleavage of E12 mAb into either single F(ab') or F(ab')$_2$ by enzymatic cleavage. Each fragment was then detected for its ability to induce Ca++flux in THP-1 cells and thereafter to induce IL-10 production in these cells.

FIG. 4 (A-H) presents inducement of IL-10 production in FOXp3-negative CD4+ T cells by E12 mAb. (A) Flow cytometry analysis of SR-BI expression on murine CD4+ T cells before and 24 h after being subjected to anti CD3&CD28 induced activation. (B) Flow cytometry analysis of IL-10 intracellular expression in CD4+ T cells from IL-10GFP donor mice when stimulated in the presence of E12 mAb, control IgG or PBS. (C) E12 mAb was cleaved into either single F(ab') or F(ab')$_2$ by enzymatic cleavage. Each fragment was then detected for its ability to inhibit IL-10 induction in murine CD+ T cells undergoing anti CD3&CD28 activation. Results are shown as mean triplicates±SE. (D) Flow cytometry analysis of FOXP3+ SR-BI+ and FOXP3– SR-BI+ subsets in on murine CD4+ T cells subjected to anti CD3&CD28 induced activation. (E) Intracellular analysis of IL-10 in FOXp3+CD4+ T cells after 48 h anti CD3&CD28 induced activation in the presence of E12 mAb or IgG1 (F) Flow cytometry analysis of the expression of CLA-1 on freshly isolated human CD4+ T cells before and after being subjected to anti CD3&CD28 induced activation. Freshly isolated human CD4+ T cells were stimulated in the presence of E12 mAb, control IgG or PBS and analyzed for IL-10 intracellular expression by flow cytometry (G), levels of IL-10 were also measured by ELISA (H). Results of one of three independent experiments with similar data are shown as mean triplicates±SE.

FIGS. 5 (A-G) presents that mAb suppresses ongoing EAE while selecting CD4+ T cells that transfer disease suppression. (A) Active EAE was induced in 6 wk old female C57BL/6 mice and on day 11, just after the onset of disease, separated into equally sick groups (6 per group) and repeatedly administered (days 11, 13 and 15) with either PBS, 300 μg of IgG1 or 300 μg of E12 mAb. Mice were monitored daily for the clinical signs of disease by an observer blind to the experimental protocol. Results are presented as mean maximal score±SE. Arrow indicates the first day of antibody treatment. (B-E). On day 18, representative mice were sacrificed CNS lumbar spinal cords were paraffin embedded, sectioned and stained with hematoxillin and eosin (B, upper panel) or subjected to Immunohistochemical staining for IL-10 (B, lower panel). Arrows indicate cells stained positive for IL-10 within the spinal cord. (C) Flow cytometry staining of spleen cells from E12 and IgG1 treated mice for CD11b+ in spleen of E12mAb treated mice and control, no difference has been observed. (D) CNS invading CD4+ T cells were analyzed for expression of SR-BI (gated on CD3) in the spleen and CNS of EAE mice (E) Flow cytometry CD4 T cell subsets analyses of CNS cells from E12 mAb and control EAE mice treated with IgG1 mice for the relative number of IL-10$^{high}$ CD4+ T cells, IL10$^{high}$SR-BI+, IL-17$^{high}$IFN-γ$^{low}$ and IL-17$^{high}$IFN-γ$^{high}$ cells. Results shown here represent three experiments with similar results (F) Donor EAE mice were subjected to repeated administrations with mAb E12 or isotype matched IgG as described above. Two days after the second injections CD4+ spleen cells were purified and transferred (30×106/mouse) to recipient EAE mice, just after the onset of disease. Mice were monitored daily for the clinical signs of disease by an observer blind to the experimental protocol. Results shown here represent three experiments with similar results and are presented as mean maximal score±SE. (G) EAE was induced in 6 wk old female wild type or IL-10–/– C57BL/6 mice. At the onset of disease four groups of equally sick WT mice, and two groups of equally sick IL10–/– mice (6 mice per group) were selected. At the onset of disease (day 11) and later on days, 13 and 15 WT mice were administered with PBS, or with 300 μg of E12, E12 F(ab') or E12 F(ab')2. IL-10–/– mice were administered with either PBS, E12 or isotype matched control IgG1. Mice were monitored daily for the clinical signs of disease by an observer blind to the experimental protocol. Results shown here represent three experiments with similar results and are presented as mean maximal score±SE. Arrow indicates the first day of antibody treatment.

FIGS. 6 (A-C) presents selection of CD4+ T cells that suppress EAE in an IL-10 dependent manner by E12 mAb. (A) E12 mAb, or control IgG1 were added to anti MOGp33-55 pre-line during the second MOGp33-55 specific stimulation cycle. After 72 h cells were analyzed for intracellular expression of various cytokines by flow cytometry. The results shown represent one of three independent experiments with similar data. (B) Each of the above pre-lines was injected (20×10$^6$ cells/mouse, iv) to recipients EAE mice at the onset of disease. Results of one of three experiments are shown as mean EAE score±SE (6 mice per group). (C) The above experimental set-up was applied, once again, with additional groups of donor mice that are IL-10–/–. Results of one of three experiments are shown as mean EAE score±SE (6 mice per group).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In an embodiment of the invention, there is provided a peptide comprising the amino acid sequence set forth in EFYSPEACRSM (SEQ ID NO: 1) or EFFSPEACRSM (SEQ ID NO: 2) or any of the functionally related peptide variants thereof.

In some embodiments of the invention, the peptide is an antigenic peptide. As used herein, in one embodiment the term "antigenic peptide" refers to a peptide that is capable of eliciting an immune response.

The peptide of the invention, in some embodiments, is obtained from an epitope on the extracellular part of the macrophage scavenger receptor B-I (SR-BI/CLA-1) protein.

In some embodiments, the peptide epitope is located between amino acid residues 273 and 283 of

SEQ ID NO: 3
(MGGSSRARWVALGLGALGLLFAALGVVMILMVPSLIKQQVLKNVRIDPS

SLSFGMWKEIPVPFYLSVYFFEVVNPNEVLNGQKPVVRERGPYVYREFRQ

KVNITFNDNDTVSFVENRSLHFQPDKSHGSESDYIVLPNILVLGGSILME

SKPVSLKLMMTLALVTMGQRAFMNRTVGEILWGYDDPFVHFLNTYLPDML

PIKGKFGLFVGMNNSNSGVFTVFTGVQNFSRIHLVDKWNGLSKIDYWHSE

QCNMINGTSGQMWAPFMTPESSLEFFSPEACRSMKLTYNESRVFEGIPTY

RFTAPDTLFANGSVYPPNEGFCPCRESGIQNVSTCRFGAPLFLSHPHFYN

ADPVLSEAVLGLNPNPKEHSLFLDIHPVTGIPMNCSVKMQLSLYIKSVKG

IGQTGKIEPVVLPLLWFEQSGAMGGKPLSTFYTQLVLMPQVLHYAQYVLL

GLGGLLLLVPIICQLRSQEKCFLFWSGSKKGSQDKEAIQAYSESLMSPAA

KGTVLQEAKL)
Or

SEQ ID NO: 4
(MGCSAKARWAAGALGVAGLLCAVLGAVMIVMVPSLIKQQVLKNVRIDPS

SLSFNMWKEIPIPFYLSVYFFDVMNPSEILKGEKPQVRERGPYVYRESRH

KSNITFNNNDTVSFLEYRTFQFQPSKSHGSESDYIVMPNILVLGAAVMME

NKPMTLKLIMTLAFTTLGERAFMNRTVGEIMWGYKDPLVNLINKYFPGMF

PFKDKFGLFAELNNSDSGLFTVFTGVQNISRIHLVDKWNGLSKVDFWHSD

QCNMINGTSGQMWPPFMTPESSLEFYSPEACRSMKLMYKESGVFEGIPTY

RFVAPKTLFANGSIYPPNEGFCPCLESGIQNVSTCRFSAPLFLSHPHFLN

ADPVLAEAVTGLHPNQEAHSLFLDIHPVTGIPMNCSVKLQLSLYMKSVAG

IGQTGKIEPVVLPLLWFAESGAMEGETLHTFYTQLVLMPKVMHYAQYVLL

ALGCVLLLVPVICQIRSQEKCYLFWSSSKKGSKDKEAIQAYSESLMTSAP

KGSVLQEAKL)

As used herein a "scavenger receptor" refers to a gene product (i.e., RNA or protein) of a scavenger receptor, which is known in the art. Examples of scavenger receptors include but are not limited to class A scavenger receptors, class B scavenger receptors and class F scavenger receptors. The scavenger receptor is expressed and displayed by macrophages in some embodiments. In some embodiments of the invention, the scavenger receptor of the present invention is SR-BI, a member of the CD36 family, GenBank Accession No. NP_005496, also known as CLA-I or SR-B1. Scavenger receptor activity refers to cell adhesion activity, transporter activity, apoptotic activity, lipid metabolism activity, signal transduction activity and/or preferably cytokine secretion activity. An effector of a scavenger receptor refers to an endogenous molecule which up-regulates or activates scavenger receptor activity. For example, an effector can be a modified lipid (e.g., oxidized lipid, glycated lipid, alkylated lipid, nitrated lipid, acetylated lipid), which binds to the scavenger receptor and activates signaling therefrom.

In an embodiment of the invention, the functionally related peptide variant of this invention comprises at least one fragment or combination of fragments, sequential or non-sequential, at a specified sequence order or in a reverse order of the sequence of the peptide set forth in SEQ ID NO: 1 or SEQ ID NO: 2.

In an embodiment of the invention, the functionally related peptide variant of this invention comprises substitution, deletion, and/or insertion at one or more positions in the peptide set forth in SEQ ID NO: 1 or SEQ ID NO: 2.

In an embodiment of the invention, the functionally related peptide variant of this invention comprises conservatively modified variants substitution at one or more positions in the peptide set forth in SEQ ID NO: 1 or SEQ ID NO: 2.

In some embodiments of the invention, the peptide may have at least 70%, 75%, 80%, 85%, 90%, 95% or 99% sequence identity to the amino acid sequence set forth in EFYSPEACRSM (SEQ ID NO: 1) or EFFSPEACRSM (SEQ ID NO: 2).

In some embodiments of the invention, the amino acids of the peptide are of L or D stereoisomers or combination thereof.

In some embodiments of the invention, this invention provides an antibody or antibody binding fragment or a functionally related variant thereof, which recognizes or forms a molecular complex with the peptide set forth in (SEQ ID NO: 1) or (SEQ ID NO: 2) or with the functionally related peptide variant thereof, wherein the peptide set forth in SEQ ID NO: 1 or SEQ ID NO: 2 or the fragment thereof is a part of the macrophage scavenger receptor protein B-I (SR-BI/CLA-1). In one embodiment of the invention, the antibody or antibody binding fragment recognizes or forms a molecular complex with at least the peptide set forth in SEQ ID NO: 1 or SEQ ID NO: 2 or part of it.

In some embodiments of the invention, the antibody binds or recognizes the peptide set forth in SEQ ID NO: 1 or SEQ ID NO: 2 or the fragment thereof, wherein the peptide is a part of the macrophage scavenger receptor protein B-I (SR-BI/CLA-1). In some embodiments of the invention, the peptide set forth in SEQ ID NO: 1 or SEQ ID NO: 2 or the fragment thereof is an epitope on the surface of the macrophage scavenger receptor protein B-I (SR-BI/CLA-1) located between amino acid residues 273 and 283 of SEQ ID NO: 3 or SEQ ID NO: 4.

In one embodiment of the invention, this invention provides a peptide comprising at least the amino acid residues that contribute most of the binding energy for a complex between the peptide set forth in SEQ ID NO: 1 or SEQ ID NO: 2 or with the functionally related peptide variants of the peptide set forth in SEQ ID NO: 1 or SEQ ID NO: 2 and an antibody or antibody binding fragment thereof.

In one embodiment, this invention provides a peptide having at least 90% homology to the peptide comprising at least the amino acid residues that contribute most of the binding energy for a complex between peptide set forth in SEQ ID NO: 1 or SEQ ID NO: 2 or with the functionally related peptide variants of the peptide set forth in SEQ ID NO: 1 or SEQ ID NO: 2 and an antibody or antibody binding fragment thereof. As used herein, the phrase "most of the binding energy" refers to the minimal number of amino acid residues that contribute altogether more than 50%, 60%, 70%, 80%, 90%, 95% of the total energy or binding affinity for the formation of a molecular complex. The single or combined energy contribution could be determined, for example, by the experimental alanine scan methodology (See, for example, Morrison et al. 2001, Curr Opin Chem Biol 5 (3): 302-7) or by computational methods to estimate thermodynamic parameters based on a theoretical alanine substitutions (See, for example, Weiss et al. 2000, Proc. Natl. Acad. Sci. U.S.A. 97 (16): 8950-4).

In another embodiment, this invention provides a peptide comprising at least the interface amino acid residues of a complex between peptide set forth in (SEQ ID NO: 1) or (SEQ ID NO: 2) or with the functionally related peptide variants of the peptide set forth in (SEQ ID NO: 1) or (SEQ ID NO: 2) and an antibody or antibody binding fragment thereof. In another embodiment, this invention provides a peptide having at least 90% sequence identity to the peptide comprising at least the interface amino acid residues of a complex between peptide set forth in (SEQ ID NO: 1) or (SEQ ID NO: 2) or with the functionally related peptide variants of the peptide set forth in (SEQ ID NO: 1) or (SEQ ID NO: 2) and an antibody or antibody binding fragment thereof. As used herein, in one embodiment of the invention, the phrase "interface amino acid residues" refer to surface residues of, for example, a molecule that has at least one atom within a certain atom distance threshold from any atoms of, for example, another molecule in a molecular complex composed of both molecules. In one embodiment, this invention provides atom distance threshold of 4, 5, 6, 7, 8, 9 or 10 angstrom.

In one embodiment of the invention, this invention provides a functionally equivalent molecule that mimics the functional activity of any of the peptide or peptide variants provided in this invention. The term "functionally equivalent molecule" refers in the application to any compound such as but not restricted to peptidomimetic or stapled peptide. The functionally equivalent molecule may be obtained by retro-inverso or D-retro-enantiomer peptide technique, consisting of D-amino acids in the reversed sequence. The functionally equivalent molecule may be obtained by using amino acid derivative.

As used herein, in one embodiment, the term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NH—G(Sc)—C(0)—Q or —OC(0)G($S_c$)—Q, wherein Q is —SR, —NRR or alkoxyl, R is hydrogen or alkyl, $S_c$ is a side chain of a naturally occurring or non-naturally occurring amino acid and G is $C_1$-$C_2$ alkyl. In certain embodiments, G is Ci alkyl and Sc is selected from the group consisting of hydrogen, alkyl, heteroalkyl, arylalkyl and heteroarylalkyl.

As used herein, in one embodiment, the term "peptide" may be derived from a natural biological source, synthesized, or produced by recombinant technology. It may be generated in any manner, including by chemical synthesis. One or more of the amino acids may be modified, for example, by the addition of a chemical entity such as a carbohydrate group, a phosphate group, a farnesyl group, an isofarnesyt group, a fatty acid group, an acyl group (e.g., acetyl group), a linker for conjugation, functionalization, or other known protecting/blocking groups.

As used herein, in one embodiment, the term "peptide," may be fragments, derivatives, analogs, or variants of the foregoing peptides, and any combination thereof. Fragments of peptides, as that term or phrase is used herein, include proteolytic fragments, as well as deletion fragments. Variants of peptides include fragments and peptides with altered amino acid sequences due to amino acid substitutions, deletions, or insertions.

Variants may occur naturally or be non-naturally occurring. Examples include fusion proteins, peptides having one or more residues chemically derivatized by reaction of a functional side group, and peptides that contain one or more naturally occurring amino acid derivatives of the twenty standard amino acids. These modifications may also include the incorporation of D-amino acids, or other non-encoded amino-acids. In one embodiment, none of the modifications should substantially interfere with the desired biological activity of the peptide, fragment thereof. In another embodiment, modifications may alter a characteristic of the peptide, fragment thereof, for instance stability or half-life, without interfering with the desired biological activity of the peptide, fragment thereof. In one embodiment, as used herein the terms "peptide" and "protein" may be used interchangeably having all the same meanings and qualities.

In one embodiment, peptide of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the peptide of the present invention and fused cleavable moiety. In one embodiment, a fusion protein can be designed so that the peptide can be readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the peptide of the present invention is retrieved in a substantially pure form.

In one embodiment, the phrase "substantially pure" refers to a purity that allows for the effective use of the protein in the applications described herein.

In one embodiment, the peptide of the present invention can also be synthesized using in vitro expression systems. In one embodiment, in vitro synthesis methods are well known in the art and the components of the system are commercially available.

In one embodiment, production of a peptide of this invention is using recombinant DNA technology. A "recombinant" peptide, or protein refers to a peptide, or protein produced by recombinant DNA techniques; i.e., produced from cells transformed by an exogenous DNA construct encoding the desired peptide or protein.

In some embodiments, the recombinant peptides, fragments thereof or peptides are synthesized and purified; their therapeutic efficacy can be assayed either in vivo or in vitro. In one embodiment, the activities of the recombinant fragments or peptides of the present invention can be ascertained using various assays including cell viability, survival of transgenic mice, and expression of megakaryocytic and lymphoid RNA markers.

In one embodiment, a peptide of this invention comprises at least 3 amino acids. In another embodiment, a peptide comprises at least 5 amino acids. In another embodiment, a peptide comprises at least 10 amino acids. In another embodiment, a peptide comprises at least 20 amino acids. In another embodiment, a peptide comprises at least 25 amino acids. In other embodiments, a peptide comprises at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists essentially of at least 5 amino acids. In another embodiment, a peptide consists essentially of at least 10 amino acids. In other embodiments, a peptide consists essentially of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists of at least 5 amino acids. In another embodiment, a peptide consists of at least 10 amino acids. In other embodiments, a peptide consists of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids.

As used herein, in one embodiment, the terms "peptide" and "fragment" may be used interchangeably having all the same meanings and qualities. As used herein in, in one embodiment the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2—NH, CH2—S, CH2—S=O, O=C—NH, CH2—O, CH2—CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Peptide bonds (—CO—NH—) within the peptide may be substituted, for example, by N-methylated bonds (—N(CH3)—CO—), ester bonds (—C(R)H—C—O—O—C(R)—N—), ketomethylen bonds (—CO—CH2—), α-aza bonds (—NH—N(R)—CO—), wherein R is any alkyl, e.g., methyl, carba bonds (—CH2—NH—), hydroxyethylene bonds (—CH(OH)—CH2—), thioamide bonds (—CS—NH—), olefinic double bonds (—CH=CH—), retro amide bonds (—NH—CO—), peptide derivatives (—N(R)—CH2—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In one embodiment, the peptide of this invention further comprises a detectable tag. As used herein, in one embodiment the term "detectable tag" refers to any moiety that can be detected by a skilled practitioner using art known techniques. Detectable tags for use in the screening methods of the present invention may be peptide sequences. Optionally the detectable tag may be removable by chemical agents or by enzymatic means, such as proteolysis. For example the term "detectable tag" includes chitin binding protein (CBP)-tag, maltose binding protein (MBP)-tag, glutathione-S-transferase (GST)-tag, poly(His)-tag, FLAG tag, Epitope tags, such as, V5-tag, c-myc-tag, and HA-tag, and fluorescence tags such as green fluorescent protein (GFP), red fluorescent protein (RFP), yellow fluorescent protein (YFP), blue fluorescent protein (BFP), and cyan fluorescent protein (CFP); as well as derivatives of these tags, or any tag known in the art. The term "detectable tag" also includes the term "detectable marker".

In one embodiment, a peptide of this invention is an isolated peptide. Such an isolated peptide may include a peptide-tag.

As used herein, in one embodiment the term "amino acid" refers to naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. As used herein, in one embodiment the phrase "Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

Antibody

In some embodiments, this invention provides an antibody or antibody binding fragment or a functionally related variant thereof.

In one embodiment, the antibody an antibody binding fragment wherein the antibody binding fragment is a single chain antibody, Fv, scFv, Fab, F(ab')$_2$, Fab', Fd, dAb, CDR, or scFv-Fc fragment, a nanobody, a minibody diabody, triabody, or a tetrabody.

In one embodiment, this antibody is a monoclonal or polyclonal antibody. In an embodiment of the invention, the antibody is an autoantibody. In some embodiments, the antibody may be a recombinant chimeric or humanized antibody.

In some embodiments, this invention provides an analog or derivative of the antibody or the antibody binding fragment thereof as described above, having at least 70%, 80%, 90% or 95% sequence identity to the amino acid sequence of the CDR regions, binding portion, functional amino acids interface residues of the antibody or antibody binding fragment. In another embodiment, this invention provides an analog or derivative of the antibody or the antibody binding fragment thereof having at least 80%, 85%, 90%, 95% homology to the amino acid content of the CDR regions, binding portion, functional amino acids interface residues of said antibody or antibody binding fragment. As used herein, in one embodiment the phrase "CDR regions" refer to the Complementarity Determining Regions which are part of the variable chains in immunoglobulins (antibodies). As used herein, in one embodiment the phrase "binding portion" refers to the antibody or the antibody binding fragment interface amino acid residues. As used herein, in one embodiment the phrase "functional amino acids interface residues" refer to the interface amino acid residues of the antibody or the antibody binding fragment that contribute most of the binding energy for the formation of a complex with the antibody.

In some embodiments, this invention provide a method for the preparation of an antibody or antibody binding fragment, wherein the method comprises the step of administering a peptide or peptide variants or peptide functionally equivalent molecule thereof to a subject and eliciting an immune response to the peptide or the peptide variants or the peptide functionally equivalent molecule. In one embodiment, the administrated peptide or peptide variants or peptide functionally equivalent molecule thereof to a subject includes also an adjuvant. In one embodiment, the administrated peptide or peptide variants or peptide functionally equivalent molecule thereof to a subject, is embedded in or connected to any molecular architecture of any type, size and atomic composition, such as proteins, peptides nucleic acids, capping groups or any combination of them.

The term "antibody" refers to whole antibody molecules as well as functional fragments thereof, such as Fab, F(ab')$_2$, and Fv that are capable of binding with antigenic portions of the target polypeptide. These functional antibody fragments constitute preferred embodiments of the present invention, and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (F(ab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule as described in, for example, U.S. Pat. No. 4,946,778.

Methods of generating antibodies are well known in the art. Purification of serum immunoglobulin antibodies (polyclonal antisera) or reactive portions thereof can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes include IgD, IgE, IgA, IgM and related proteins.

Methods of generating and isolating monoclonal antibodies are well known in the art, as summarized for example in reviews such as Tramontano and Schloeder, Methods in Enzymology 178, 551-568, 1989. A recombinant scavenger receptor polypeptide may be used to generate antibodies in vitro (see Example 6 of the Examples section which follows). In general, a suitable host animal is immunized with the recombinant polypeptide. Advantageously, the animal host used is a mouse of an inbred strain. Animals are typically immunized with a mixture comprising a solution of the recombinant polypeptide in a physiologically acceptable vehicle, and any suitable adjuvant, which achieves an enhanced immune response to the immunogen. By way of example, the primary immunization conveniently may be accomplished with a mixture of a solution of the recombinant polypeptide and Freund's complete adjuvant, said mixture being prepared in the form of a water in oil emulsion. Typically the immunization will be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the polypeptide can be determined during the immunization schedule by any convenient method including by way of example radioimmunoassay, or enzyme linked immunosorbant assay, which is known as the ELISA assay. When suitable antibody titers are achieved, antibody-producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multi-well plates, and the culture supernatants are screened to identify cultures containing antibodies that recognize the hapten of choice. Hybridomas that secrete antibodies that recognize the recombinant polypeptide are cloned by limiting dilution and expanded, under appropriate culture conditions. Monoclonal antibodies are purified and characterized in terms of immunoglobulin type and binding affinity.

Antibody fragments according to the present invention can be prepared by proteolytic hydrolysis of the antibody or by expression in $E.$ $coli$ or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, in U.S. Pat. Nos. 4,036,945 and 4,331,647, and references contained therein, which patents are hereby incorporated by reference in their entirety (see also Porter, R. R., Biochem. J., 73: 119-126, 1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al. (Proc. Nat'l Acad. Sci. USA 69:2659-62, 1972). Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as $E.$ $coli$. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, all of which are hereby incorporated by reference in its entirety.

Another form of an antibody fragment is a peptide coding for a single complementarity-determining region (CDR). CDR peptides ("minimal recognition units") can be obtained by constructing CDR genes encoding the CDR of an antibody of interest. Such genes are prepared, for example, by using the polymerase chain reaction to synthesize the variable region from RNA of antibody-producing cells (see, for example, Larrick and Fry Methods, 2: 106-10, 1991).

Humanized forms of non-human (e.g., murine) antibodies are chimeric molecules of immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art (see also Example 6 of the Examples section). Generally, a humanized antibody has one or more amino acid residues introduced into it from a source, which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human monoclonal antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Peptides or antibodies or antibodies binding fragments of the present invention can be synthesized using solid phase peptide synthesis procedures which are well known in the art and further described by John Morrow Stewart and Janis Dillaha Young, Solid Phase Peptide Syntheses (2nd Ed., Pierce Chemical Company, 1984). Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the polypeptides are desired, they can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al. (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

As used herein, the phrases "antibody that selectively binds" or "antibody that specifically binds" means that the antibody reacts or associates more frequently, more rapidly, with greater duration, with greater affinity, or with some combination of the above to an epitope or to a peptide of the current invention or to the scavenger receptor than with alternative substances, including unrelated proteins. "Selectively binds" or "specifically binds" means, for instance, that an antibody binds to a protein with a KD of at least about 0.1 mM, but more usually at least about 1 µM. In some embodiments the KD may be 0.01 µM or better.

Polynucleotide

In some embodiments of the invention, there is provided a polynucleotide encoding a peptide comprising the amino acid sequence set forth in EFYSPEACRSM (SEQ ID NO: 1) or EFFSPEACRSM (SEQ ID NO: 2) or any of the functionally related peptide variants thereof provided herein. In some embodiments this invention, there is provided a plasmid or a vector comprising a polynucleotide which encodes a peptide comprising the amino acid sequence set forth in EFYSPEACRSM (SEQ ID NO: 1) or EFFSPEACRSM (SEQ ID NO: 2) or any of the functionally related peptide variants thereof provided herein.

In some embodiments of the invention, there is provided a polynucleotide encoding an antibody or antibody binding fragment and related variants thereof as provided herein. In some embodiments, this invention provides a plasmid or a vector comprising a polynucleotide that encodes an antibody or antibody binding fragment and related variants thereof provided herein.

In one embodiment, the nucleic acid molecules, antibodies, antibody binding fragment and/or peptides of this invention may be an isolated nucleic acid molecule, an isolated antibody, an isolated antibody binding fragment and an isolated peptide.

As used herein, in one embodiment the term "isolated" means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for example for mutagenesis, to form fusion proteins, to form expression vectors, to form tagged proteins or peptides, for in vitro expression, and for propagation or expression in a host. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides, polypeptides and peptides may occur in a composition, such as a media, formulations, solutions for introduction of polynucleotides, polypeptides or peptides, for example, into cells, compositions or solutions for chemical or enzymatic reactions, for instance, which are not naturally occurring compositions, and, therein remain isolated polynucleotides or polypeptides within the meaning of that term as it is employed herein.

As used herein, in one embodiment the term "nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof.

A nucleic acid "backbone" may be made up of a variety of linkages, including one or more of sugar-phosphodiester linkages, peptide-nucleic acid bonds), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., The Biochemistry of the Nucleic Acids 5-36, Adams et ah, ed., 11th ed., 1992; Abraham et al, 2007, BioTechniques 43: 617-24), which include derivatives of purine or pyrimidine bases (e.g., N4-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, 06-methylguanine, 4-thio-pyrimidines, 4-amino-pyrimidines, 4-dimethylhydrazine-pyrimidines, and 04-alkyl-pyrimidines, and pyrazolo-compounds, such as unsubstituted or 3-substituted pyrazolo[3,4-d]pyrimidine). Nucleic acids may include "abasic" residues in which the backbone does not include a nitrogenous base for one or more residues.

A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et ah, Biochemistry 43: 13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid. As used herein, in one embodiment the terms "nucleic acid molecule", "polynucleotide" and "nucleotide" may be used interchangeably having all the same meanings and qualities.

As used herein, in one embodiment the term "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-0-Me). As used herein, methoxy oligonucleotides containing "T" residues have a methoxy group at the 2' position of the ribose moiety, and a uracil at the base position of the nucleotide.

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, the term "nucleic acid" or "oligonucleotide" refers to a molecule, which may include, but is not limited to, prokaryotic sequences, eukaryotic mRNA, cDNA from eukaryotic mRNA, genomic DNA sequences from eukaryotic (e g , mammalian) DNA, and even synthetic DNA sequences. The term also refers to sequences that include any of the known base analogs of DNA and RNA.

The nucleic acids can be produced by any synthetic or recombinant process, which are well known in the art. Nucleic acids can further be modified to alter biophysical or biological properties by means of techniques known in the art. For example, the nucleic acid can be modified to increase its stability against nucleases (e.g., "end-capping"), or to modify its solubility, or binding affinity to complementary sequences. These nucleic acids may comprise the vector, the expression cassette, the promoter sequence, the gene of interest, or any combination thereof. In another embodiment, its lipophilicity may be modified, which, in turn, will reflect changes in the systems employed for its delivery, and in one embodiment, may further be influenced by whether such sequences are desired for retention within, or permeation through the skin, or any of its layers. Such considerations may influence any compound used in this invention, in the methods and systems described.

In one embodiment, DNA can be synthesized chemically from the four nucleotides in whole or in part by methods known in the art. Such methods include those described in Caruthers (1985; Science 230:281-285). DNA can also be synthesized by preparing overlapping double-stranded oligonucleotides, filling in the gaps, and ligating the ends together (see, generally, Sambrook et al. (1989; Molecular Cloning—A Laboratory Manual, 2nd Edition. Cold Spring Habour Laboratory Press, New York)). In another embodiment, mutations may be prepared from wild-type DNA by site-directed mutagenesis (see, for example, Zoller et al. (1982; DNA. 1984 December; 3(6):479-88); Zoller (1983); and Zoller (1984; DNA. 1984 December; 3(6):479-88); McPherson (1991; Directed Mutagenesis: A Practical Approach. Oxford University Press, NY)). The DNA obtained can be amplified by methods known in the art. One suitable method is the polymerase chain reaction (PCR) method described in Saiki et al. (1988; Science. 1988 Jan. 29; 239(4839):487-491), Mullis et al., U.S. Pat. No. 4,683, 195, and Sambrook et al. (1989).

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. Variations in DNA sequences, which are caused by point mutations or by induced modifications (including insertion, deletion, and substitution) to enhance the activity, half-life or production of the polypeptides encoded thereby, are also encompassed in the invention.

As will be appreciated by one skilled in the art, a fragment or derivative of a nucleic acid sequence or gene that encodes for a protein or peptide can still function in the same manner as the entire wild type gene or sequence. Likewise, forms of nucleic acid sequences can have variations as compared to wild type sequences, nevertheless encoding the protein or peptide of interest, or fragments thereof, retaining wild type function exhibiting the same biological effect, despite these variations. Each of these represents a separate embodiment of this present invention.

In some embodiments, this invention provides an isolated polynucleotide encoding the peptide or the peptide variants of this invention. In some embodiments, this invention provides a plasmid or any other vector comprising an isolated polynucleotide encoding the peptide or peptide variants of this invention.

In some embodiments, this invention provides an isolated polynucleotide encoding the antibody or the antibody binding fragment of this invention. In some embodiments, this invention provides a plasmid or any other vector comprising an isolated polynucleotide encoding the antibody or the antibody binding fragment of this invention.

In one embodiment, the term "vector" or "expression vector" refers to a carrier molecule into which a nucleic acid sequence can be inserted for introduction into a cell where it can be replicated. In one embodiment, the nucleic acid molecules are transcribed into RNA, which in some cases are then translated into a protein, polypeptide, or peptide. In one embodiment, expression vectors can contain a variety of "control sequences" which refer to nucleic acid sequences necessary for the transcription and possibly translation of an operably linked coding sequence in a particular host cell. In another embodiment, a vector further includes an origin of replication. As used herein, the term "control sequence" may also be referred to herein as a "regulatory sequence". In one embodiment the vector may be a shuttle vector, which in one embodiment can propagate both in prokaryotic and eukaryotic cells, or in another embodiment, the vector may be constructed to facilitate its integration within the genome of an organism of choice.

As used herein, the terms "vector" and "expression vector" may be used interchangeably having all the same meanings and qualities. In one embodiment, as used herein the term "expression vector" refers to a DNA construct comprising an essential control component which is operably linked to an insert gene so that the insert gene is only expressed when introduced into the host cell. In another embodiment, the term "expression vector" refers to a DNA construct comprising an essential control component which is operably linked to an insert gene so that the insert gene is may be expressed in an in vitro expression system as is known in the art. The expression vector may be prepared and purified by a standard recombinant DNA technology. The type of the expression vector is not particularly limited, as long as it may express and produce a target gene, in vitro and/or in a variety of host cells of prokaryotic and eukaryotic cells. In one embodiment, the expression vector is a vector capable of producing a large amount of a recombinant protein, which may be a protein or peptide or antibody or antibody binding fragment of this invention, in a similar form to the native protein or peptide or antibody or antibody binding fragment while it retains a strong promoter activity and a strong expression ability. The expression vector is preferably a vector comprising at least a promoter, a start codon, a gene encoding a target protein, a stop codon, and a terminator. In addition, it may comprise a DNA encoding a signal peptide, an enhancer sequence, untranslated regions at the 5' and 3' ends of a target gene, a selectable marker region or a replicable unit, etc., if desired. Moreover, the type of the expression vector may be a mono-cistronic vector including a polynucleotide encoding one recombinant protein, a bi-cistronic vector including a polynucleotide encoding two recombinant proteins, a poly-cistronic vector including a polynucleotide encoding three recombinant proteins or more. In one embodiment, a promoter is a Vav promoter.

The vector, in other embodiments may be, for example, a plasmid, a bacmid, a phagemid, a cosmid, a phage, a virus or an artificial chromosome. In one embodiment, the vector is a viral vector, which in one embodiment may be a bacteriophage, mammalian virus, or plant virus.

In one embodiment, the viral vector is an adenoviral vector. In another embodiment, the adenovirus may be of any known serotype or subgroup. In another embodiment, the viral vector is an adeno associated viral vector. In another embodiment, the adenoviral vector is a helper-dependent adenoviral vector ("HDAD", "HD" or "HDAd" or "HD-Ad"), which in another embodiment, is synonymous with gutless, gutted, mini, fully deleted, high-capacity, Δ, or pseudo adenovirus, and which in another embodiment are deleted of all viral coding sequences except for sequences supporting DNA replication, which in one embodiment, comprise the adenovirus inverted terminal repeats and packaging sequence (Ψ). In another embodiment, helper-dependent adenoviruses express no viral proteins.

In another embodiment, the viral vector is an adeno associated viral vector. In another embodiment, the viral vector is a retroviral vector.

In other embodiments, the viral vector is derived from a virus such as vaccinia virus, lentivirus, polio virus, hepatitis virus, papilloma virus, cytomegalovirus, simian virus, or herpes simplex virus.

In certain embodiments of the invention, the vector comprising a nucleic acid sequence may comprise naked recombinant DNA or plasmids. Transfer of the construct may be performed by any method which physically or chemically permeabilizes the cell membrane. In one embodiment, the vector is a mini-circle DNA, which in one embodiment, is a supercoiled DNA molecule for non-viral gene transfer, which has neither a bacterial origin of replication nor an antibiotic resistance marker. In another embodiment, mini-circle DNA comprises no bacterial control regions from gene delivery vectors during the process of plasmid production. They are thus smaller and potentially safer than other plasmids used in gene therapy. In one embodiment, mini-circle DNA produce high yield, are simple to purify, and provide robust and persistent transgene expression.

Construction of vectors using standard recombinant techniques is well known in the art (see, for example, Maniatis, et al., Molecular Cloning, A Laboratory Manual (Cold Spring Harbor, 1990) and Ausubel, et al., 1994, Current Protocols in Molecular Biology (John Wiley & Sons, 1996), both incorporated herein by reference).

In one embodiment, a vector comprising a nucleic acid encoding a therapeutic peptide or antibody or antibody biding fragment of the instant invention is introduced into a host cell. There are a number of techniques known in the art for introducing cassettes and/or vectors into cells, for affecting the methods of the present invention, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation or liposome-mediated transfection, (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals).

In one embodiment, bombardment with nucleic acid coated particles may be a method for transferring a naked DNA expression construct into cells. This method depends on the ability to accelerate DNA-coated micro-projectiles to a high velocity allowing them to pierce cell membranes and enter cells without killing them. Several devices for accelerating small particles have been developed. One such device relies on a high voltage discharge to generate an electrical current, which in turn provides the motive force. The micro-projectiles used have comprised biologically inert or biocompatible substances such as tungsten or gold beads. It is to be understood that any of these methods may be utilized for introduction of the desired sequences into cells, and cells thereby produced are to be considered as part of this invention, as is their use for effecting the methods of this invention.

The efficacy of a particular expression vector system and method of introducing nucleic acid into a cell can be assessed by standard approaches routinely used in the art as described herein below.

Any one of a number of different vectors can be used, such as viral vectors, plasmid vectors, linear DNA, etc., as known in the art, to introduce an exogenous nucleic acid fragment encoding a peptide or protein or antibody or antibody binding fragment into target cells. These vectors can be inserted, for example, using infection, transduction, transfection, calcium-phosphate mediated transfection, DEAE-dextran mediated transfection, electroporation, liposome-mediated transfection, biolistic gene delivery, liposomal gene delivery using fusogenic and anionic liposomes (which are an alternative to the use of cationic liposomes), direct injection, receptor-mediated uptake, magnetoporation, ultrasound, or any combination thereof, as well as other techniques known in the art (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). The polynucleotide segments encoding sequences of interest can be ligated into an expression vector system suitable for transducing mammalian cells and for directing the expression of recombinant products within the transduced cells. Once the exogenous nucleic acid fragment has been incorporated into the cells using any of the techniques described above or known in the art, the production and/or the secretion rate of the therapeutic agent encoded by the nucleic acid fragment can be quantified. In one embodiment, the term "exogenous" refers to a substance that originated outside, for example a nucleic acid that originated outside of a cell or tissue.

In one embodiment, this invention provides a host cell transfected with a vector of this invention. In one embodiment the host cell may be a prokaryotic or eukaryotic cell. In one embodiment, the prokaryotic cell may be a bacterial cell. In one embodiment, the eukaryotic cell may be a fungal cell, a plant cell or an animal cell. In one embodiment, an animal cell is a human cell.

In one embodiment, nucleic acids of this invention are comprised in a vector. In one embodiment, a nucleic acid of this invention encodes a peptide or antibody or antibody binding fragment thereof of the current invention. In another embodiment a nucleic acid of this invention encodes a fragment of the peptide or antibody or antibody binding fragment thereof of the current invention. In yet another embodiment, a nucleic acid encodes a full length peptide or antibody or antibody binding fragment thereof of the current invention which further comprises a tag element. In some embodiments, the vector of and for use in a method of the present invention comprise a nucleic acid sequence operably linked to one or more regulatory sequences, wherein said nucleic acid sequence encodes peptide or antibody or antibody binding fragment thereof of the current invention. In another embodiment, the vector consists essentially of such a nucleic acid sequence, and in another embodiment, the vector consists of such a nucleic acid sequence.

Pharmaceutical Composition

Another aspect of the present invention relates to a pharmaceutical composition including a pharmaceutically acceptable carrier and an active ingredient. The phrase "active ingredient" refers to any of the peptides, the fragments thereof, the functionally equivalent molecule that mimics the functional activity of the peptide, the an antibody or an antibody binding fragment or a polynucleotide encoding a peptide or encoding an antibody or encoding an antibody binding fragment according to the embodiments of the present invention. The active ingredient could have an agonist or antagonist activity or both. The pharmaceutical composition can contain one or more of the above-identified active ingredients of the present invention. Typically, the pharmaceutical composition of the present invention will include an active ingredient of the present invention, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of an active ingredient, together with the adjuvants, carriers and/or excipients. While individual needs may vary, determination of optimal ranges of effective amounts of each active ingredient, is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the active ingredient thereof of the present invention, can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the active ingredient thereof of the present invention, and a carrier, for example, lubricants and inert fillers such as, lactose, sucrose, or cornstarch. In another embodiment, the active ingredient is tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate. The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the active ingredient can be incorporated with excipients and used in the form of tablets, capsules, elixirs, suspensions, syrups, and the like. Such compositions and preparations should contain at least 0.1% of active ingredient thereof. The percentage of the compound in these compositions can, of course, be varied and can conveniently be between about 2% to about 60% of the weight of the unit. The amount of active ingredient thereof in such therapeutically useful compositions is such that a suitable dosage will be obtained. Preferred compositions according to the present invention are prepared so that an oral dosage unit contains between about 1 mg and 800 mg of active ingredient thereof.

The active ingredient of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The active ingredient thereof or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

This active ingredient may also be administered parenterally. Solutions or suspensions of these active ingredients thereof can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the active ingredient thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

When administering the active ingredient of the present invention, and pharmaceutical compositions thereof, they can be administered systemically or, alternatively, they can be administered directly to a specific site. Thus, administering can be accomplished in any manner effective for delivering the active ingredients thereof or the pharmaceutical compositions to the specific targeted cells. Exemplary modes of administration include, without limitation, administering the active ingredients thereof or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Determination of a therapeutically effective amount of an active ingredient peptide is well within the capability of those skilled in the art, especially in light of the detailed disclosure provided herein.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

It is further understood that the active ingredient of the invention can be formulated or administered together with additional active ingredients as required to treat the condition of the patient.

Method of Treating

In one embodiment, this invention is directed to a method of treating, suppressing, reducing the severity, reducing the risk of developing or inhibiting an autoimmune disease comprising administering the active ingredient of the invention, which include the peptide, the fragment thereof, the functionally related peptide variant, the antibody, or the nucleic acids as described herein to a subject suffering from an autoimmune disease under conditions effective to treat the autoimmune disease.

In one embodiment, the invention provides active ingredient and compositions comprising the same, for use in treating, suppressing, reducing the incidence, reducing the severity, or inhibiting the progression of autoimmune diseases, inflammatory diseases or neuroinflammatory diseases in a subject. In another embodiment, the compositions may further comprise additional active ingredients, the activity of which is useful for the particular application for which the polypeptides, fragments thereof and peptides thereof are being administered.

In one embodiment, this invention is directed to a method of treating, suppressing, reducing the severity, reducing the risk of developing or inhibiting an inflammatory and/or autoimmunity and/or neuroinflammation disease comprising administering a therapeutically effective amount of active ingredient of the invention as hereinafter described, which includes a peptide, a fragment thereof, a functionally related peptide variant, an antibody, or a nucleic acid as described herein, to a subject suffering from an inflammatory and/or autoimmunity and/or neuroinflammation disease, under conditions effective to treat the autoimmune disease.

In one embodiment, "treatment" or "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, the term "about", refers to a deviance of between 0.0001-5% from the indicated number or range of numbers. In one embodiment, the term "about", refers to a deviance of between 10% from the indicated number or range of numbers.

A number of diseases and conditions, which typically cause inflammatory response in individuals can be treated using the methodologies and pharmaceutical composition described hereinabove. Examples of such diseases and conditions are summarized infra.

Inflammatory diseases—Include, but are not limited to, chronic inflammatory diseases and acute inflammatory diseases.

Inflammatory diseases associated with hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci U S A 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci U S A 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, Th1 lymphocyte mediated hypersensitivity and Th2 lymphocyte mediated hypersensitivity.

Autoimmune diseases include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost.2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome, diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl:S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E.

and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

Inflammatory diseases can affect the central nervous system (brain and spinal cord). Some of the best characterized disorders are multiple sclerosis (MS) and various forms of meningitis and encephalitis. A common feature of these diseases is a disruption of the blood-brain barrier (BBB) followed by inflammatory perivascular infiltration and eventual demyelination and astrogliosis.

In one embodiment, this invention provides a method of reducing an inflammatory response in a subject, the method comprising providing to a subject in need thereof a therapeutically effective amount of the pharmaceutical composition comprising the active ingredient as hereinafter defined.

In one embodiment, this invention provides a method for treating an autoimmune disease, the method comprising providing to a subject in need thereof a therapeutically effective amount of pharmaceutical composition comprising the active ingredient of the invention. In some embodiments, the autoimmune disease is IBD or multiple sclerosis.

In one embodiment, this invention provides a method of preventing graft rejection comprising providing to a subject in need thereof a therapeutically effective amount of pharmaceutical composition comprising the active ingredient of the invention. In another embodiment, this invention provides a method of preventing graft rejection comprising providing to a subject in need thereof a therapeutically effective amount of pharmaceutical composition described herein. In some embodiments, the graft rejection is graft vs. host disease (GVHD).

A Method for Screening of Compounds Capable of Mimicking the Structure or Functional Activity of the Peptide of the Current Invention In one embodiment, the structure or functional activity of the peptide of this invention may be used as a template for screening other compounds capable of mimicking the structure or functional activity of the peptide of the current invention. Such screening methodologies are well known in the art, for example High-throughput screening (Zhang et al. 2011. Cambridge University Press). For example as disclosed in International Application Publication No. WO 2013/054193 and Hughes et al (2011) British Journal of Pharmacology, 162 1239-1249. For example, methods known in the art are utilized to generate a population of 3D structures of the peptide (in their bioactive conformations). From these 3D structures, a consensus field pharmacophore (a molecular framework that describes the essential features responsible for a molecule's biological activity) may be constructed from a population of peptides of this invention that may recognize or binds to the scavenger receptor. A consensus field pharmacophore may be considered a consensus version of the molecular fields and/or field points from a series of molecules that are known to bind at the same target, keeping molecular fields/field points that are common between the molecules and eliminating those that vary (as they are not essential for or may be deleterious to binding). Such selection of field points may be informed by the properties of the peptides of this invention. A consensus field pharmacophore can be also obtained for example by applying alanine scan methodologies which are well known in the art, for the peptide of the current invention. The alanine scan approach enables to locate the most functionally dominated amino acids along the peptide sequence.

Combinatorial chemistry may be used to prepare a large number (tens to thousands or even millions) of compounds in a single process. These compound libraries can be made as mixtures, sets of individual compounds or chemical structures generated in computer, for example for virtual screening (Rester et al. U 2008, *Curr Opin Drug Discov Devel* 11 (4): 559-68.). The consensus field pharmacophore data may then be used for screening such libraries in order to allow identification of possible useful novel components of the libraries, The novel chemical compounds identified may then be synthesized and tested for their in vitro and in vivo properties with respect to the ability of the novel chemical compound to recognize or binds to the antibody or antibody binding fragment of the current invention, or to compete with the peptide of the current invention on binding to the antibody or antibody binding fragment of the current invention.

Diagnosis

In an embodiment of the invention, there is provided a method for detecting the severity of an autoimmune and/or neuroinflammation and/or allergic disease, providing a prognosis, or detecting a subject at risk for developing an inflammatory and/or autoimmunity and/or neuroinflammation and/or allergic disease by detecting the amount of an antibody to scavenger receptor in a test sample comprising: a) contacting a test sample from the individual with at least one capture molecule, wherein the capture molecule is the peptide or peptide variants according to the embodiments of this invention or any functionally equivalent molecule of the peptide or peptide variants of this invention; and b) detecting binding of the antibody to scavenger receptor in the test sample to said capture molecule, thereby detecting the presence or the amount of the antibody to scavenger receptor in the test sample. In some embodiments, the severity of the multiple sclerosis disease could be detected.

As used herein, the term "subject" refers to any animal (e.g., a mammal), including, but not limited to, humans, non-human primates, rodents, and the like, which is to be the recipient of a particular treatment. Typically, the terms "subject", "individual" and "patient" are used interchangeably herein in reference to a human subject.

As used herein, the subject may be a subject suspected of having an inflammatory and/or autoimmunity and/or neuroinflammation and/or allergic disease. For example a subject that is suspected of having a multiple sclerosis disease. The term "subject suspected of having an inflammatory and/or autoimmunity and/or neuroinflammation and/or allergic disease refers to a subject that presents one or more symptoms indicative of an inflammatory and/or autoimmunity and/or neuroinflammation and/or allergic disease or is being screened for any of these diseases. A subject suspected of having any of these diseases may also have one or more risk factor. However, a subject suspected of having any of these diseases encompasses an individual who has received an initial diagnosis but for whom the severity of the disease is not known. The term further includes people who once had any of these diseases in the past, but whose symptoms have ameliorated.

As used herein, the term "subject at risk for an inflammatory and/or autoimmunity and/or neuroinflammation and/or allergic disease refers to a subject with one or more risk factors for developing an inflammatory and/or autoimmunity and/or neuroinflammation and/or allergic disease. Risk factors include, but are not limited to, gender, age, genetic predisposition, environmental expose, previous incidents of these diseases and lifestyle.

As used herein, the term "providing a prognosis" refers to providing information regarding the impact of the presence of an inflammatory and/or autoimmunity and/or neuroinflammation and/or allergic disease (e.g., as determined by the diagnostic methods of the present invention) on a subject's future health (e.g., expected morbidity or mortality).

In another embodiment of the invention, the determination of level of scavenger receptor autoantibodies or fragments thereof may be used in a method for detecting the susceptibility of an individual or subject to develop disease or condition attributable to inflammation and/or autoimmunity and/or neuroinflammation. The method for detecting comprises the step of measuring the level of scavenger autoantibodies or any fragments thereof in a blood sample from the individual or subject that bind to the peptide set forth in SEQ ID NO: 1 or SEQ ID NO: 2 or to any peptide provided by the current invention or to any functionally equivalent molecule of the peptide provided by the current invention, wherein if the level is higher than the level of a normal individual or subject, or to the level obtained in previous tests within the same subject, the individual or subject is at risk to develop disease or condition attributable to inflammation and/or autoimmunity and/or neuroinflammation. In some embodiments, the disease or condition attributable to inflammation and/or autoimmunity and/or neuroinflammation is multiple sclerosis.

By a "normal individual" or "normal subject" it is meant an average level of some healthy individuals or subjects that do not show clinical symptoms of the disease, which serves as a control. The level of the antibodies in healthy individuals or subjects as opposed to ill individuals or subjects, can be determined by one skilled in the art by any assay using a capture molecule and a detector molecule to quantify captured molecules. Examples of immunoassays useful in the disclosure include, but are not limited to, radioimmunoassay (RIA), fluoroluminescence assay (FLA), chemiluminescence assay (CA), enzyme-linked immunosorbant assay (ELISA) and the like. The capture molecule can be in an embodiment of the invention, as the peptide as set forth in SEQ ID NO: 1 or SEQ ID NO: 2, or any peptide variants provided by this invention or any functionally equivalent molecule of the peptide or peptide variants provided by this invention and any fragments thereof. Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Immunoassay

Assay systems utilizing a capture molecule and a detector molecule to quantify captured molecules are well known. Examples of immunoassays useful in the disclosure include, but are not limited to, radioimmunoassay (RIA), fluoroluminescence assay (FLA), chemiluminescence assay (CA), enzyme-linked immunosorbant assay (ELISA) and the like.

The immunoassay can be a solid phase assay, a liquid phase assay, and the like.

The immunoassay, in one embodiment, may be designed for an automated, high-throughput instrument. For example, the Access® family of instruments by Beckman Coulter, Inc. are well suited to effectuate the immunoassay of the disclosure. The Access®. Immunoassay System allows for rapid throughput of up to 100 tests per hour through the use of a reaction vessel loader that has the capacity for up to three hours of continuous sample processing.

In another embodiment, the quantity of target molecule bound to the capture molecule can be determined using a competitive binding assay. In one embodiment, a capture molecule and a horseradish peroxidase (HRP)-labeled scavenger receptor antibody are used to determine concentration. After removal of unbound label by washing, the HRP signal can be expressed. HRP may be detected by reacting HRP with a calorimetric substrate and measuring the optical density of the reacted substrate at a 450 nm absorbance. The concentration of scavenger receptore antibody present in the test sample will be proportional to the signal expressed.

In an embodiment of the invention, the epitope or peptide or functionally equivalent molecule of the peptide according to the current invention recognized by the antibody to scavenger receptor is immobilized on a solid support.

For a solid-phase immunoassay, the capture molecule is immobilized to a solid support. The solid phase used for immobilization may be any inert support or carrier that is essentially water insoluble and useful in immunometric assays, including supports in the form of, e.g., surfaces, particles, porous matrices, etc. Examples of commonly used supports include small sheets, SEPHADEX® gels, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Capture molecules can also be immobilized on a substrate, such as a polymeric bead, colloidal metal or iron oxide particle. Beads can be plastic, glass, or any other suitable material, typically in the 1-20 micron range. In some embodiments, paramagnetic beads are used. Colloidal metal particles such as colloidal gold and silver particles and iron oxide particles can be prepared using many different procedures commercially available or otherwise known to those skilled in the art.

In one embodiment, the immobilized capture molecules are coated on a microtiter plate, and in another embodiment the solid phase is a multi-well microtiter plate that can analyze several samples at one time. The solid phase is coated with the capture molecules as defined above, which may be linked by a non-covalent or covalent interaction or physical linkage, as desired.

Commonly used cross-linking agents for attaching the capture molecules to the solid-phase substrate include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters, such as 3,3'-dithiobis(succinimidylpropionate), and bifunctional maleimides, such as bis-N-maleimido-1,8-octane. Derivatizing agents, such as methyl-3-((p-azidophenyl)-dithio)propioimidate yield photoactivatable intermediates capable of forming cross-links in the presence of light.

The coated plates are then typically treated with a blocking agent that binds non-specifically with and saturates the unoccupied binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, typically about 1.5 to 3 hours.

After coating and blocking, the calibrator formulations (known concentrations of the antibody to scavenger receptor that act as calibrators) or the test sample to be analyzed, appropriately diluted, are added to the immobilized phase. Commonly, the dilution rate is about 0.001-15% (v/v). In some embodiments of the invention, the dilution rate is 0.05-5%. In some embodiments of the invention, the dilution rate is 0.1-1%.

The amount of capture molecule employed is sufficiently large to give a good signal in comparison with the calibration standards, but is generally not in molar excess compared to the maximum expected level of the scavenger receptor antibodies. For sufficient sensitivity, the amount of test sample should be added such that the immobilized capture molecules are in molar excess of the maximum molar concentration of free analyte of interest anticipated in the test sample after appropriate dilution of the sample. This anticipated maximum level depends mainly on any known correlation between the concentration levels of the antibody of interest in the particular test sample being analyzed and the clinical condition of the patient.

Generally, the conditions for incubation of sample and immobilized capture molecule are selected to maximize analytical sensitivity of the assay to minimize dissociation, and to ensure that sufficient analyte of interest that is present in the sample binds with the immobilized capture molecule. It is understood that the selection of optimum reaction conditions generally requires only routine experimentation. The incubation is accomplished at fairly constant temperatures, ranging from about 0° C. to about 40° C., generally at, or about, room temperature. The time for incubation is generally no greater than about 10 hours. The duration of incubation may be longer if a protease inhibitor is added to prevent proteases in the test sample from degrading the antibody of interest.

The detector molecule can be labeled with any detectable marker that does not interfere with the binding of the captured analyte to the detecting agent. Examples of suitable label moieties include moieties that may be detected directly, such as fluorochrome, chemiluminescent, colorimetric, energy transfer agents and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase bacterial luciferase, luciferin, 2,3-dihydrophthalazinediones, HRP, alkaline phosphatase, amylase, catalase, lactamase, hexokinase, urease, malate dehydrogenase, P-galactosidase, glucoamylase, lysozyme, saccharide oxidases, e.g., glucose oxidase, galactose oxidase, and glucose-6-phosphate dehydrogenase, heterocyclic oxidases, such as uricase and xanthine oxidase, coupled with an enzyme that employs hydrogen peroxide to oxidize a dye precursor such as HRP, lactoperoxidase, or microperoxidase, biotin/avidin, biotin/streptavidin, biotin/Streptavidin-p-galactosidase with 4-methylumbelliferyl-d-galactosidase (MUG), spin labels, bacteriophage labels, stable free radicals, and the like.

Conjugation of the label moiety to the detection molecule, such as, for example, an antibody, is a standard manipulative procedure in immunoassay techniques.

In an embodiment of the invention, the amount of scavenger receptor antibody bound to the capture molecule can be determined by washing away unbound detection molecule from the immobilized phase, and measuring the amount of detection molecule bound to the analyte using a detection method appropriate to the label. The label moiety can be, for example, an enzyme. In the case of enzyme moieties, the amount of developed signal, for example, color, is a direct measurement of the amount of captured analyte. For example, when HRP is the label moiety, color is detected by quantifying the optical density (O.D.) at 450 nm absorbance. In another embodiment, the quantity of analyte bound to the capture molecule can be determined indirectly. The signal of an unlabeled detection molecule may be amplified for detection with a detection molecule-specific antibody conjugated to a label moiety. For example, the signal of an unlabeled mouse antibody that binds with the analyte may be amplified with a mouse IgG-specific sheep antibody labeled with HRP. The label moiety is detected using a detection method appropriate for the label. For example, HRP may be detected by reacting HRP with a calorimetric substrate and measuring the optical density of the reacted substrate at 450 nm absorbance.

The method also provides the quantification of individual scavenger receptor antibody levels in a test sample and correlation of these levels to a disease condition. In one embodiment, the relative levels of the individual scavenger receptor antibody in a test sample are determined and said levels are correlated to the presence of, or propensity for, a specific disease condition.

Kits

As a matter of convenience, the assay method of this disclosure can be provided in the form of a kit. Such a kit is a packaged combination comprising the basic elements of:

(a) at least one capture molecule which is the peptide or peptide variants of this invention or any functionally equivalent molecule of the peptide or peptide variants of this invention that specifically binds to at least one scavenger receptor antibody; (b) at least one detector molecule that binds with at least one scavenger receptor antibody; and (c) instructions on how to perform the assay method using these reagents.

In another embodiment, this invention further provides a kit to aid in measuring the level of an antibody that binds to the scavenger receptor, comprising at least one capture molecule which is any peptide provided by this invention or any functionally equivalent molecule of the peptide provided by this invention and at least one detector molecule. In one embodiment the kit provided by this invention further comprises a detectable label.

In one embodiment the kit provided by this invention is used for detecting the susceptibility of an individual or subject to develop disease or condition attributable to inflammation and/or autoimmunity and/or neuroinflammation by measuring the level of autoantibodies in a blood sample of the individual or subject. In another embodiment the kit provided by this invention is used for diagnosis or prognosis of inflammation and/or autoimmunity and/or neuroinflammation related diseases of an individual by measuring the level of autoantibodies in a blood sample of the individual or subject.

In one embodiment of the invention, the kit may further provide calibrators of the scavenger receptor antibody useful in the correlation with specific an inflammatory and/or autoimmunity and/or neuroinflammation and/or allergic disease conditions.

In another embodiment, the kit further comprises a solid support for the capture molecules, which may be provided as a separate element or as an element on which the capture molecules are already immobilized. Hence, the capture molecules in the kit either may be immobilized already on a solid support, or may become immobilized on a support that is included with the kit or provided separately from the kit. The solid support may be a microtiter plate, a colloidal metal particle, an iron oxide particle, and a polymeric bead.

The detector molecules may be labeled molecules (e.g. antibodies) detected directly or unlabeled molecules that are detected by labeled antibodies directed against the unlabeled antibodies raised in a different species. Where the label is an enzyme, the kit will ordinarily include substrates and cofactors required by the enzyme, where the label is a fluorophore, a dye precursor that provides the detectable chromophore, and where the label is biotin, an avidin such as avidin, streptavidin, either alone or conjugated to a chromophore. In another embodiment of the invention, the detector may be a chemiluminescent agent, a colorimetric agent, an energy transfer agent, a substrate of an enzyme reaction, a fluorescent agent or a radioisotope.

The kit may further include an instructions sheet, describing how to carry out the assay of the kit.

EXAMPLES

Experimental Methods

Study Population: The MS group included 36 subjects suffering from early stage disease (3 months to 10 years, average 4.53 years), and 23 age-matched healthy controls. In all subjects diagnosis was confirmed by MRI. Patient demographics and characteristics were determined according the 2005 revisions to the McDonald Diagnostic criteria for MS (Polman et al. 2005, Ann Neurol 58, 840-846) and are specified in Table I. Sera of 7 patients were drawn during ongoing attack, whereas all others during remission. The RA group consisted of 25 patients (19 F/6 M, mean age 42, age range 16-64) with rheumatoid factor positive (seropositive), erosive rheumatoid arthritis. All patients fulfilled ACR criteria for RA. Disease duration range was 1-4 years. During the sampling time 18 patients were on various NSAID' s, low steroid therapy (maximum dose 10 mg/day), and had not yet been subjected to disease-modifying drugs such as Methotrexate, Plaquenil, Imuran, or Solganal (gold injections). The other seven patients were treated with Methotrexate (15 mg/week). None were treated with anti-TNF-$\alpha$ preparations. The viral encephalitis control group included 6 age-matched subjects.

Blood samples from healthy donors: Blood samples from healthy donors for in vitro proliferation assays were purchased from the Israel Blood Bank (MDA, Tel Aviv, Israel). All donors signed a consent stating that their blood samples can be used for medical research.

Mice: 6 wk old female C57BL/6 mice were purchased from Harlan (Jerusalem, Israel). IL-10$^{-/-}$ mice were purchased from The Jackson Laboratory (Bar Harbor, Me.). Foxp3-GFP reporter mice (Bettelli et al. 2006, The Journal of clinical investigation 116, 2393-2402) were kindly provided by V. Kuchroo (Harvard Medical School, Boston, Mass.). Animals were maintained under specific pathogen-free conditions in our animal facility. The local Technion ethics committee for experiments in animals approved all animal experimental work. Breeders of IL-10-GFP reporter mice (Madan et al. 2009. Journal of immunology 183, 2312-2320) were previously obtained from Christopher Karp (the Bill & Melinda Gates Foundation, Seattle, USA) and recently used to delineate the role of CXCL11 in directing T cell polarization (Meiron et al. 2008, J Exp Med. 205, 2643-2655).

Cloning of human and murine receptors (extra-cellular domains): Human cDNA encoding the extracellular domains of CLA-1, CD14, SR-A or CD36 was generated by RT-PCR from RNA extracted from THP-1 (human monocytic cell line) cells, cultured for 4 days with LPS. Likewise, cDNA encoding the extracellular domains of murine receptors VCAM-1, CCR5, CCR2, and CXCR4 was generated from RAW264.7 (Mouse leukaemic monocyte macrophage cell line), under the same conditions. Primers were designed according the published sequence of each gene product and are listed below.

```
CLA-1 (SEQ ID NO: 5): Sense -
GGAATTCCATATGGAGATGAACGTGCGCATCGACCCCAGT;

anti-sense (SEQ ID NO: 6) -
CCCAAGCTTCTGAGTGTAGAATGTGTGAAGA.

hCD14 (SEQ ID NO: 7): Sense -
GCTGATATCGCCCCACCAGAGCCCTGCGAG;

anti-sense (SEQ ID NO: 8) -
CCCAAGCTTTCAAGCTCCGGCGGTGACTAC.

mCD14 (SEQ ID NO: 9): Sense -
CCCAAGCTTATGGAGCGTGTGCTTGGCTTG;

anti-sense (SEQ ID NO: 10) -
CGCGGATCCTTAAACAAAGAGGCGATCTCC hSR-A (SEQ ID NO: 11): Sense -
GCTGACACTTGGGAAATGAAGAACTGCTTA;

anti-sense (SEQ ID NO: 12) -
CCCAAGCTTTCATGAAGTACAAGTGACCCC.

mSR-A (SEQ ID NO: 13): Sense -
GCTGACACTTGGGAAATGAAGAACTGCTTA;

anti-sense (SEQ ID NO: 14) -
CCCAAGCTTTCATGAAGTACAAGTGACCCC hCD36 (SEQ ID NO: 15): Sense -
GCTGATATCGGAGACATGCTTATTGAGAAG;

anti-sense (SEQ ID NO: 16) -
CCCAAGCTTTCACACAGGCTTTCCTTCTTT.

mSR-BI: Sense (SEQ ID NO: 17) -
GCTGATATCATCCATCTGGTGGATAAGTG;

anti-sense (SEQ ID NO: 18)-
CCCAAGCTTTCAGATCCCAGTGACCGGGT mCD36 (SEQ ID NO: 19): Sense -
CCCAAGCTTATGGGCTGTGATCGGAACTGT anti-sense (SEQ ID NO: 20):
CGCGGATCCTTATTTTCCATTCTTGGATTT mCCR2 (SEQ ID NO: 21): Sense -
CCCAAGCTTATGGAAGACAATAATATGTTAC anti-sense (SEQ ID NO: 22):
CCGCTCGAGCACACTGGTTTTATGACAAGGC mCCR5 (SEQ ID NO: 23): Sense -
CCCAAGCTTAGATCTCAGAAAGAAGGTTT;

anti-sense (SEQ ID NO: 24) -
CCGCTCGAGCTTTAATGTTTGGAAACTCT mVCAM-1 (SEQ ID NO: 25): Sense -
GCTGATATCTTTAAAATCGAGATCTCCCC ;

anti-sense (SEQ ID NO: 26) -
CCGGAATTCTCAAGAGTGCTCATCCTCAA
```

Expression and purification of recombinant proteins: PCR products were recloned into a pET-30a (Novagen, Inc) expression vector, expressed as 6xHis-tagged proteins in BL21 (DE3) E. coli, and then purified by Ni-NTA super flow affinity purification (Qiagen). After purification, protein purity was verified by gel electrophoresis followed by sequencing (N terminus) by our sequencing service unit.

Generation of monoclonal antibodies: Anti SR-BI mAbs (E12 mAb) were generated in BALB/C mice according the basic protocol described in (Harlow et al. 1988, Cold Spring Harbor Laboratory, New York).

Evaluation of antibody titer in Serum Samples: Ab titers were determined by a direct ELISA assay as described elsewhere (Wildbaum et al. 2003, Immunity 19, 679-688). Briefly, 96 wells ELISA plates (Nunc, Roskilde, Denmark) were, or were not, coated with 50 ng/well of recombinant proteins, and were blocked with 5% BSA. Sera were added either in serial dilutions or at a dilution of 1:500 (OD 450 measurement). Bound antibodies were detected using HRP-conjugated goat anti-mouse IgG antibody (Jackson ImmunoResearchLaboratories) and the soluble substrate, TNBS (DakoCytomation, Carpinteria, Calif.). Titer was determined by comparing the OD measured in wells coated with the appropriate recombinant proteins (extracellular domains of receptors) to those not coated with this recombinant protein.

Anti-CLA-1/SR-BI polyclonal autoantibody purification: Polyclonal anti-CLA-1/SR-BI autoantibodies were affinity purified from pooled sera using G protein columns followed by NHS-bound recombinant CLA-1/SR-BI columns. Purified antibodies were analyzed for binding to CLA-1/SR-BI using flow cytometry and western blot analysis.

Epitope mapping: Two panels of either 11AA or 13AA overlapping peptides were synthesized according the amino acid sequence of the extracellular domain of SR-BI/CLA-1. Autoantibodies and E12 mAb were tested for their ability to bind each peptide by direct ELISA.

Induction of active and adoptively transferred disease: EAE was induced by immunizing mice with MOGp35-55/CFA, as described by Tompkins et al (Tompkins et al. 2002, Journal of immunology 168, 4173-4183). Animals were then monitored daily for clinical signs by an observer blind to the treatment protocol. Adoptive disease was induced as described elsewhere (Goldberg et al. 2004, Journal of immunology 173, 6465-6471), with the modification of using MOGp35-55-specific line cells. EAE was scored as follows: 0, clinically normal; 1, flaccid tail; 2, hind limb paralysis; 3, total hind limb paralysis, accompanied by an apparent front limb paralysis; 4, total hind limb and front limb paralysis, 5, death.

DNA vaccination: Cloned SR-BI and CD36 (murine) constructed into pcDNA3 were used for targeted DNA vaccination. Before being administered during ongoing EAE both vaccines were tested by being injected into naive C57BL/6 mice. Four to five days later, RT-PCR was applied on tibialis anterior muscle samples to verify that the relevant insert of each gene is transcribed in the injected muscle. Only then each vaccine was used during ongoing EAE according the protocol described in detail elsewhere.

Cell separation: Spinal cords were digested for 4 h with 300U/ml type IV collagenase (Wothington, Lakewood N.J.) in DMEM. Cells were then separated by Ficoll, washed and stained.

Flow cytometry: Flow cytometry analysis was conducted according to the protocol described in detail elsewhere (Sapir et al. 2010, Journal of immunology 185, 2589-2599). For intracellular staining, the Cytofix/Cytoperm kit and anti-mouse IL-4, IL-10, IL-17 and IFN-γ antibodies, as well as anti-CD4 mAb (clone L3T4) for gating on CD4$^+$ cells, were all purchased from BD Biosciences. The FOXp3/CD4/CD25 flow cytometry kit was purchased from BioLegend, San Diego, Calif. SR-BI$^+$/CLA-1$^+$ cells were stained using Rabbit anti SR-BI/Cla1 (# NB400-101SS, Novus Biologicals, Ittleton, Co.). Dylight405-labeled donkey anti Rabbit IgG antibody was used as secondary antibody. Gating included subtraction of binding of the Dylight405-labeled Ab alone. These results were also verified using E12 mAb as primary antibody, and APC-labeled goat anti mouse IgG antibody as secondary antibody (not shown). For technical reasons commercial antibody for flow cytometry analyses was used.

Histopathology: The lumbar spinal cord was dissected, fixed in 4% paraformaldehyde, dehydrated, and embedded in paraffin. Next, 5-μm thick sections were stained with H&E. Each section was evaluated for tissue damage and mononuclear infiltration using the following scale: 0, no mononuclear cell infiltration; 1, one to five perivascular lesions per section with minimal parenchymal infiltration; 2, five to 10 perivascular lesions per section with parenchymal infiltration; and 3, >10 perivascular lesions per section with extensive parenchymal infiltration.

Immunohistochemistry: Lumbar spinal cords were dissected, fixed in 4% paraformaldehyde, dehydrated and embedded in paraffin. Sections (5 μm thick) mounted on Superfrostslides, were blocked using normal Donkey serum (Jackson ImmunoResearch Laboratories, West Grove, Pa.). Slides were then subjected to immunohistochemistry analysis using goat anti IL-10 antibody (R&D Systems, Minneapolis, Minn.). Donkey anti goat biotinylatedAb (Jackson ImmunoResearch Laboratories) was used as a secondary Ab, followed by streptavidin-conjugated peroxidase (Zymed-LabratoriesInc, San Francisco, USA). AEC (ZymedLabratoriesInc) was then used as a substrate.

Statistical analysis: The significance of differences was examined using Student's t-test. P values smaller than 0.05 were considered statistically significant.

Analyses of autoantibody titers in MS subjects was conducted according to (Leman E S et al. Cancer Research 2007, 67(12), 5600-5605). The cut-off was determined using ROC curve analysis that is based on the binomial distribution to obtain upper and lower bounds for 95% confidence intervals surrounding estimates of test sensitivity and specificity (Leman E S et al. Cancer Research 2007, 67(12), 5600-5605).

Patient Demographics and Characteristics:

TABLE 1

Patient demographics and characteristics: MS patient demographics and characteristics was determined according the 2005 revisions to the McDonald Diagnostic criteria for MS (Polman et al. 2005, Ann Neurol 58, 840-846).

| | |
|---|---|
| Number of patients enrolled | 57 |
| Relapsing-remitting | 52 |
| Relapsing-progressive | 5 |
| Age | 39.75 ± 11.46 (19 ÷ 67 y) |
| Female | 38 |
| Male | 19 |
| Duration of disease | 7.1 ± 5.95 (3 mo-32 y) |
| Disease severity (at time of first visit): | |
| EDSS <3.0 | 43 |
| EDSS <4.5 | 12 |
| EDSS >4.5 | 2 |
| Patients in remission during follow-up period (01.08-08.11) | 24 |
| Patients with relapse during follow-up period (01.08-08.11) | 25 |
| Patients after relapse (one visit) | 8 |
| Treatment (in the end of study) | 51 |
| Avonex (Interferon β-1a IM) | 12 |
| Betaferon (Interferon β-1b SC) | 16 |
| Rebif (Interferon β-1a SC) | 20 |
| Copaxone (GA) | 1 |
| Tyzabri (Natalizumab) | 2 |
| No treatment (in the end of study) | 6 |

EDSS = Expanded Disability Status Scale.

Example 1

Figure 1A:
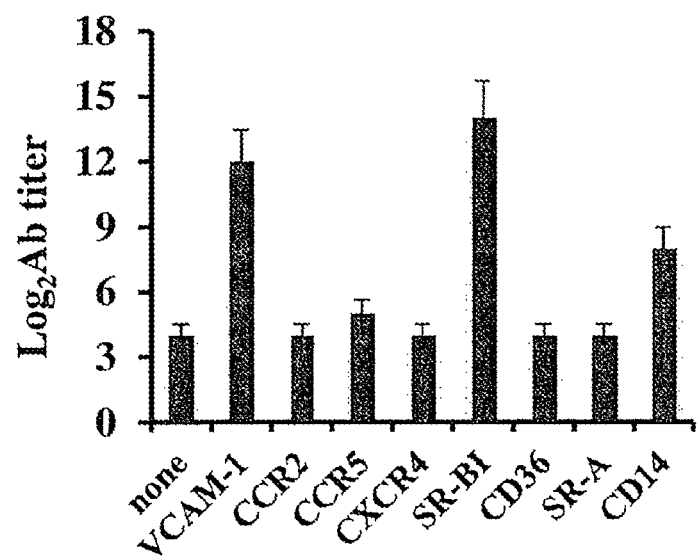
FIG. 1 A presents a graph showing autoantibody titer developed in EAE mice at the onset of disease. Results of sera of six mice are shown as mean Log2Ab titer±SE (triplicates).
Figure 1B:
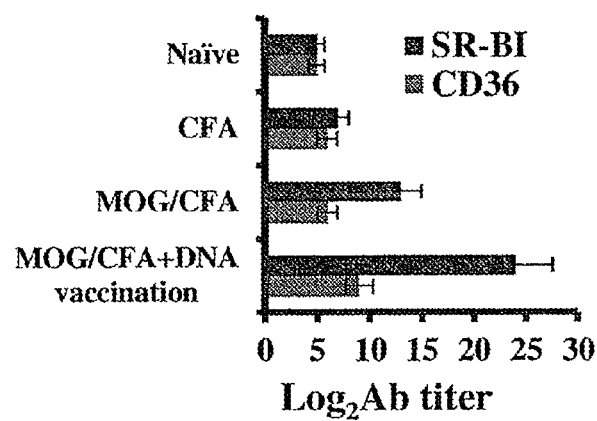

EAE Mice Exhibit an Autoantibody Response to SR-BI that, when Amplified, Suppresses an Ongoing Disease In a screen to identify autoantibodies produced during active EAE, the extracellular domains of various chemokine receptors, adhesion receptors and SRs was cloned. Purified recombinant proteins were used to coat ELISA plates for the subsequent detection of the antibody response to each receptor in the screen by direct ELISA. EAE was induced in mice by injecting them with MOGp33-55/CFA. At the onset of disease, serum was extracted and antibody titers were determined. FIG. 1A shows that EAE mice displayed an autoantibody response to the adhesion receptor VCAM-1 ($\log_2$Ab titer of 12±1 compared to 4±0.5,), SR-BI ($\log_2$Ab titer of 14±1.2 compared to 4±0.5,) and CD14 ($\log_2$Ab titer of 8±0.66 compared to 4±0.5,), but not to SR-A, CD36, CCR2, CCR5 and CXCR4. To amplify the production of SR-BI autoantibodies during active EAE, MOGp33-55/CFA-treated mice were administered with plasmid DNA encoding SR-BI using the targeted DNA vaccination method. As negative controls, mice were either administered with CD36-expressing plasmid or an empty vector. At the peak of disease, antibody titers to SR-BI and CD36 were determined in each group. FIG. 1B shows that the selective autoantibody response generated in EAE mice against SR-BI was successfully amplified by the targeted DNA plasmid (>2,000 fold amplification). Interestingly, these mice displayed a significantly lower manifestation of disease (FIG. 1C, mean maximal score 0.66±0.1 compared to 3±0.26,), suggesting that the amplified SR-BI autoantibodies suppress the ongoing disease.

To further test this hypothesis, the capability of SR-BI autoantibodies of suppressing EAE was tested in adoptive transfer experiments. Polyclonal anti-SR-BI autoantibodies were affinity purified from pooled sera obtained from MOGp33-55/CFA-treated mice injected with the SR-BI-encoding plasmid. Affinity purification was performed in two steps, using a protein G column followed by an NHS-bound recombinant SR-BI column. As negative controls, IgG1 was purified from EAE mice injected with the CD36-encoding plasmid, empty vector or PBS.

Figure 1C:
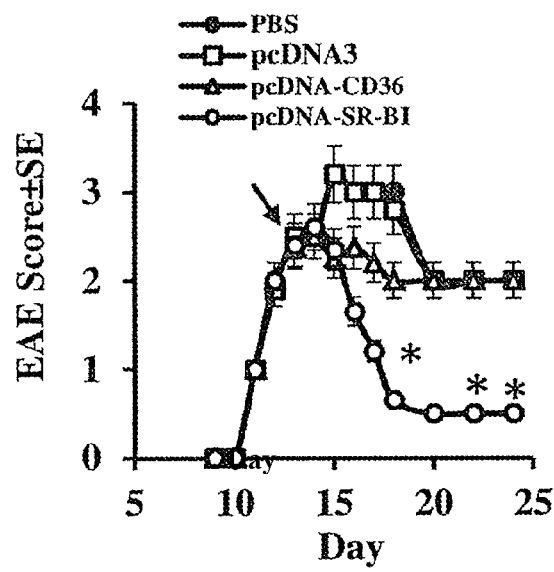
Figure 1D:
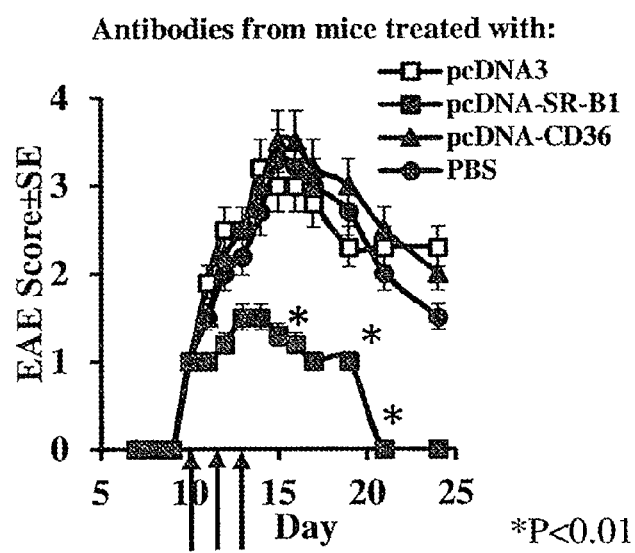

Antibodies were injected to recipient EAE mice (300 μg/mouse) at the onset of disease, every other day, three times. FIG. 1D shows that mice injected with anti SR-BI purified autoantibodies went into fast remission with no residual sign of disease within 10 days after receiving antibody therapy (,whereas the disease continued to progress in the three control groups. Epitope mapping of the target to which the anti SR-BI polyclonal antibodies bind revealed a single linear 11AA epitope encompassed between AA 273 to 283 of the protein (273-EFFSPEACRSM-283) within the extracellular domain (FIG. 1E).

The following overlapping peptides were used for the epitope mapping as shown in columns 1-9 in FIG. 1E:

```
1.
                                        (SEQ ID NO: 27)
IHLVDKWNGLSEVKYWHSEQCNMINGTAGQMWAPFMTPESSLEF

FSPEACRSMKLTYQESGVFE (whole extracellular domain)

2.
                                        (SEQ ID NO: 28)
IHLVDKWNGLS 3.
                                        (SEQ ID NO: 29)
VDKWNGLSEV 4.
                                        (SEQ ID NO: 30)
SEVKYWHSEQC 5.
                                        (SEQ ID NO: 31)
EQCNMINGTAG 6.
                                        (SEQ ID NO: 32)
TAGQMWAPFMT 7.
                                        (SEQ ID NO: 33)
FMTPESSLEFF 8.
                                        (SEQ ID NO: 34)
EFFSPEACRSM 9.
                                        (SEQ ID NO: 35)
RSMKLTYQES 10.
                                        (SEQ ID NO: 36)
QESGVFE
```

The targeted DNA vaccines encoding this gene amplify the response to the very same epitope. Gene bank analyses showed no similarity to any known gene product. This epitope is highly conserved and differs from that in the human homologue, CLA-1, by a single AA at position 275 (substitution of F to Y). Thus far, our findings demonstrate that during EAE the immune system selectively generates autoantibodies to a unique epitope on SR-BI/CLA-1 that are likely to participate in the regulation of autoimmunity.

Example 2

Figure 2B:
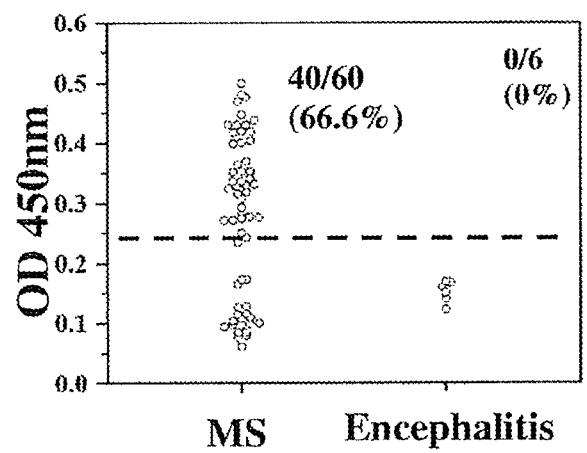
Figure 2C:
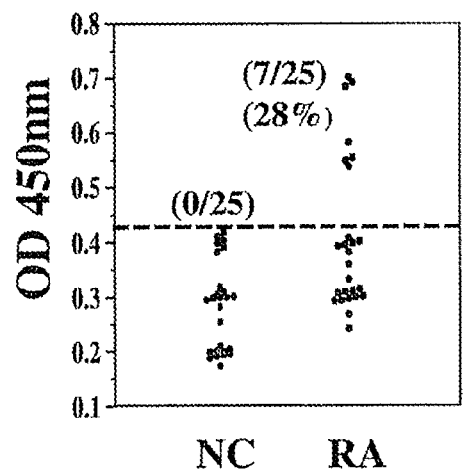
Figure 2D:
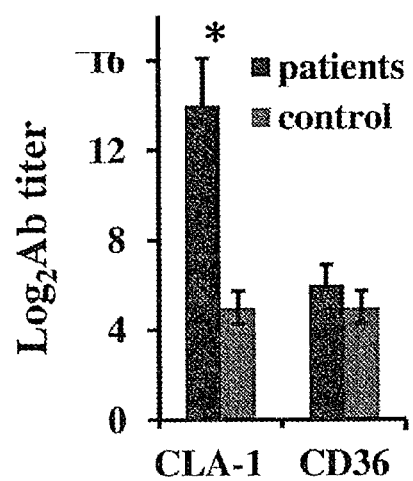

Anti CLA-1 Autoantibodies Against the 273-283 AA Epitope are Present in the Sera of MS Patients To explore the relevance of our findings to human disease, the antibody response to CLA-1 in the sera of multiple sclerosis (MS) patients was assessed. The study included 60 MS patients with demographic characteristics as described in Table 1. The vast majority of the patients (55/60) were diagnosed with relapsing-remitting MS and 5 others with relapsing progressive MS. Age matched healthy volunteers (23) and patients with viral encephalitis (6) served as control groups. Antibody response was determined at a single sera dilution of 1:500 using ELISA. FIG. 2A shows that almost 70% of MS patients displayed a significant antibody response to CLA-1 (68.3% compared to 4.3% in healthy controls), but not SR-A (8.3%) or CD36 (6.6%). Similarly to EAE mice (FIG. 1) an autoantibody response to CD14 in the MS subjects could be detected (23%). Patients with viral encephalitis did not mount any antibody response to CLA-1 (FIG. 2B, 0/6), ruling out the possibility that the autoantibody response is a result of brain inflammation. To check whether anti CLA-1 antibody production could be associated with other inflammatory autoimmune diseases, autoantibody production to CLA-1 in RA patients was assessed. The RA group consisted of 25 patients with rheumatoid factor positive, erosive rheumatoid arthritis, all fulfilling the ACR criteria for RA, with disease duration of 1-4 years. About 30% of these patients (FIG. 2C) develop autoantibodies to CLA-1. Thus anti CLA-1 autoantibodies are also detectable in other autoimmune diseases, though not in the same ratio. Quantification of the autoantibody titer in human MS patients (FIG. 2D) revealed a comparable titer (14±1) to that of EAE mice (FIGS. 1A-B). This relatively low titer, unless extensively amplified by targeted DNA vaccines, is insufficient to prevent or markedly suppress the development of EAE in mice (FIG. 1C). It is thus conceivable that in MS patients, at this low titer, they are incapable of preventing the development of disease, but might participate in its regulation.

Figure 2E:
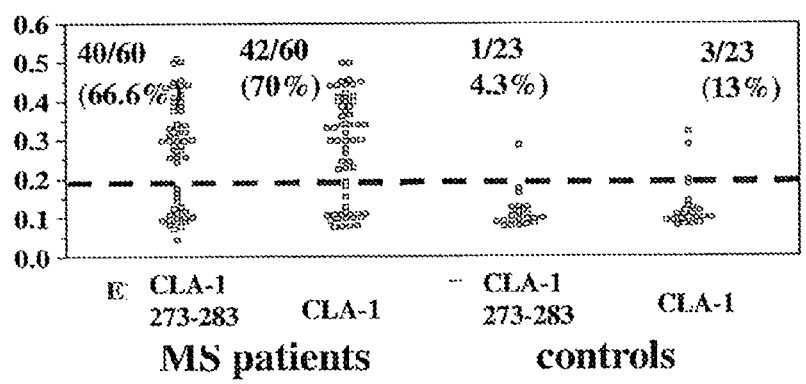

The anti CLA-1 antibodies in MS patients were tested to assess whether they are directed against the 11AA acid epitope EFYSPEACRSM, similarly to mice autoantibodies. FIG. 2E shows that vast majority of subjects that displayed an autoantibody response to CLA-1 produced antibodies to this particular epitope.

Example 3

Anti-SR-BI/CLA-1 Autoantibodies Possess Anti-Inflammatory Properties

Figure 2F:
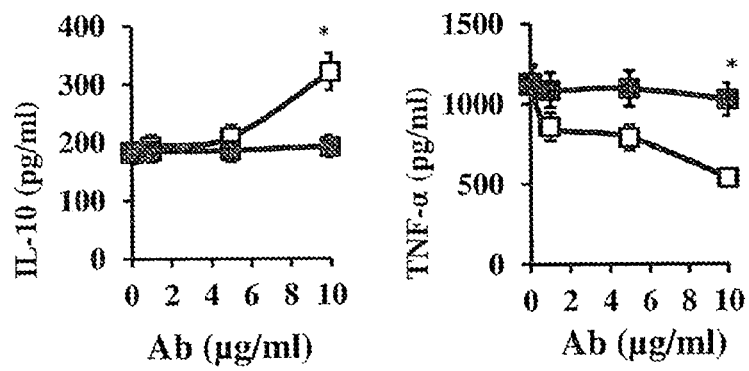
Figure 2G:
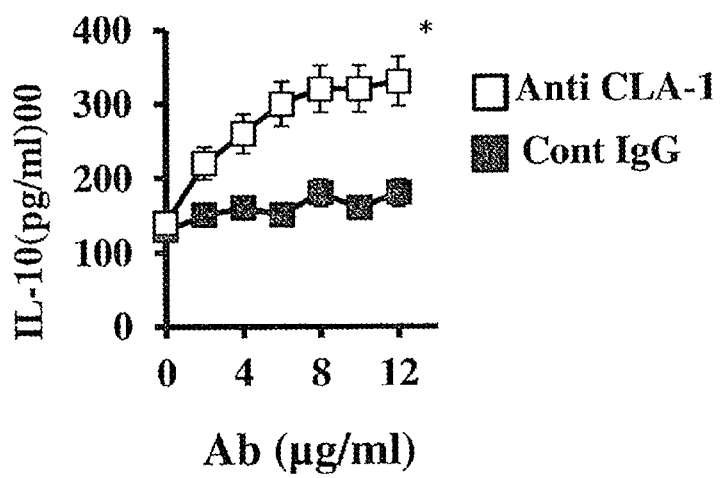

Next, the mechanism underlying the regulatory, and possibly protective, role of the autoantibodies was explored. PMA-induced macrophage-like THP-1 cells were pre-incubated with 0.5 μg/ml LPS, and 5 hours later, increasing concentrations of polyclonal anti-CLA-1 autoantibodies purified from pooled MS sera were added. After 48h, IL-10 and TNF-α levels were measured in the culture medium using standard ELISA method. Cultures supplemented with 10 μg/ml antibody showed an increase in IL-10 production and a reciprocal decrease in TNF-α (FIG. 2F). To examine if they might have a direct effect on CD4+ cells CD4+ T cells were isolated from PBL of three different healthy individuals and subjected to anti CD3 (1 μg/ml) and anti CD28 (1 μg/ml) induced activation. After 2h, E12 mAb was added at different concentrations and the level of IL-10 in the culture medium was measured 48 h later using standard ELISA method. In all samples levels of IL-10 were significantly increased in the presence of E12 mAb (FIG. 2G). These findings highlight the anti-inflammatory properties of the anti-CLA-1 antibodies supporting the hypothesis that they participate in the regulation of MS in a beneficial manner.

Example 4

E12 mAb Drives the Polarization of Macrophages to $CD11b^+CD206^+IL10^{high}$ by Binding its Target Epitope A monoclonal antibody named E12 mAb was generated to the 11AA recognized by these autoantibodies and studied the effect of this mAb (IgG1) was tested on macrophage and CD4+ polarization and biological function.

Figure 3E:
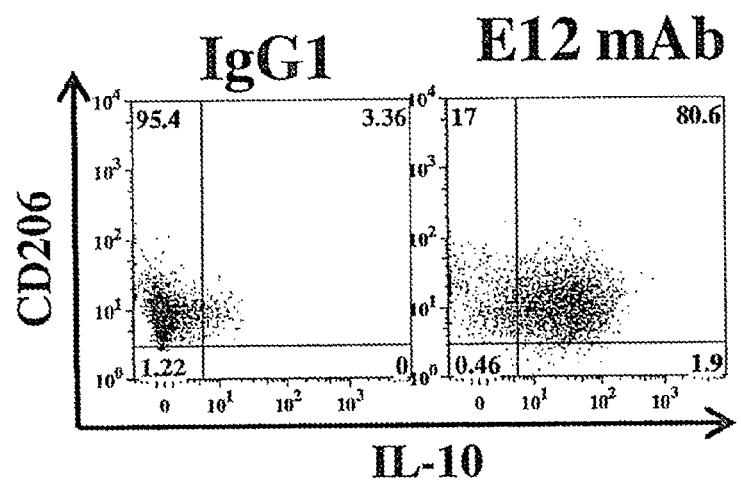
Figure 3F:
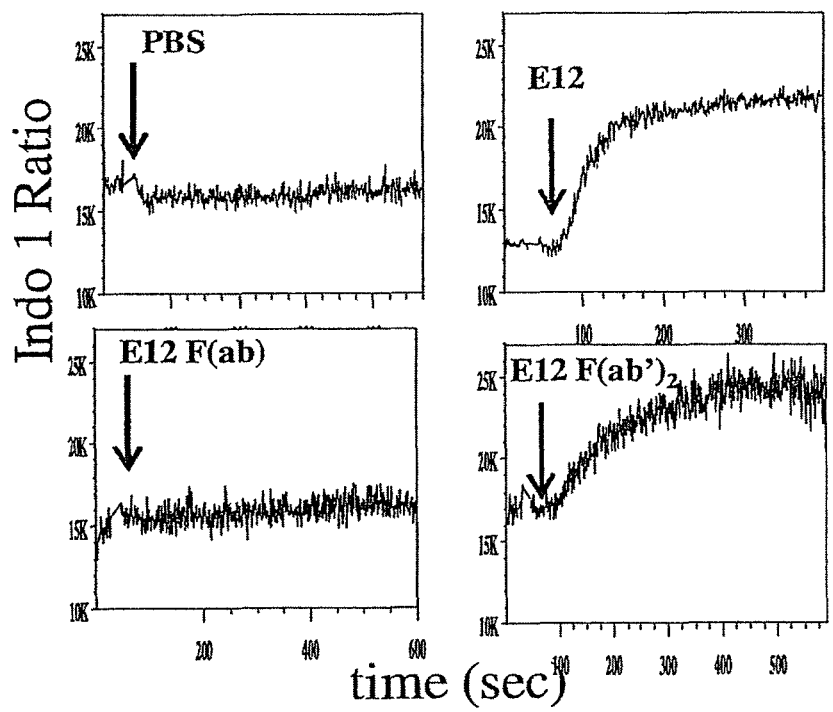
Figure 3G:
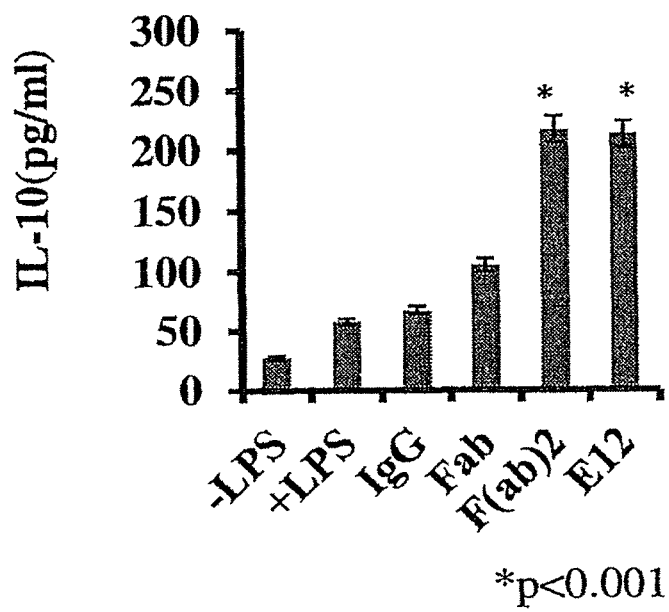

First flow cytometry analysis was used to verify the expression of SR-BI on CD11b+ peritoneal macrophages of C57BL6 mice before and after LPS (1 μg/ml) induced activation. The results show that the vast majority of these cells are SR-BI+ and that at a concentration of 1 μg/ml LPS, they do not internalize this receptor (FIG. 3A). Then the binding of E12 mAb to its target receptor on peritoneal macrophages affects their polarization and biological function was assessed. In these experiments macrophages from IL-10GFP reporter mice (Zohar et al. 2014, The Journal of clinical investigation 124, 2009-2022) activated in vitro with 0.1 μg/ml LPS that binds SR-B1, or 1 μg/ml Zymosan, that does not bind SR-B1 were used. The latter is an insoluble preparation of cell wall from Saccharomyces cerevisiae that activates macrophages via TLR2 and Dectin-1 (Dillon et al. 2006, The Journal of clinical investigation 116, 916-928). E12 mAb induced a dose dependent induction of IL-10 and reduction in TNF-α and IL-12 in both LPS- and Zymosan-activated macrophages (FIGS. 3B-C). Next the mechanistic basis by which E12 mAb affects the biological properties of macrophages was investigated. CD11b+CD206+ cells are a subset of M2 alternatively activated macrophages that possess anti-inflammatory properties (Gundra et al. 2014, Blood 123, e110-122) FIG. 3D shows that LPS activated peritoneal macrophages hardly express CD206 (only about 0.25%) and that in the presence of E12 mAb the number of CD11b+CD206+ cells increases to 6.16%. Further analysis shows that in the presence of E12 mAb, the vast majority of these cells (80.6%) are $CD11b+CD206+IL-10^{high}$ (FIG. 3E). To explore the possibility that the E12 mAb acts as an agonist of its target receptor, it was cleaved into either single F(ab) or F(ab')$_2$ by enzymatic cleavage (Rousseaux et al. 1983, J Immunol Methods 64, 141-146). Each fragment was then analyzed for its ability to induce Ca++flux (Grynkiewicz et al. 1985, The Journal of biological chemistry 260, 3440-3450) as well as IL-10 production in THP-1 cells. The native mAb as well as its F(ab')$_2$ fragment, but not the single chain F(ab), induced Ca++flux (FIG. 3F) as well as IL-10 production (FIG. 3G) in the target cells. Collectively, these results suggest that the E12 mAb acts as an agonist of its target receptor and that its anti-inflammatory properties are due, in part, to its ability to polarize macrophages to $CD11b+CD206+IL-10^{high}$ cells.

Example 5

Figure 4A:
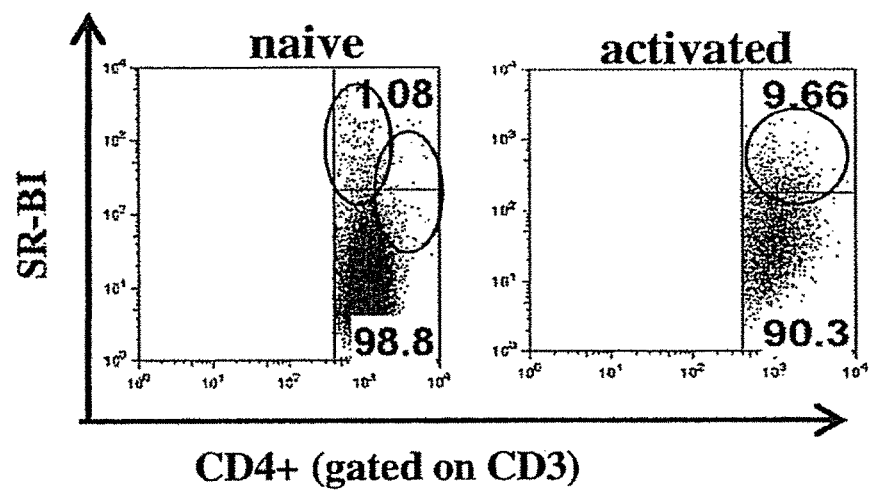
Figure 4B:
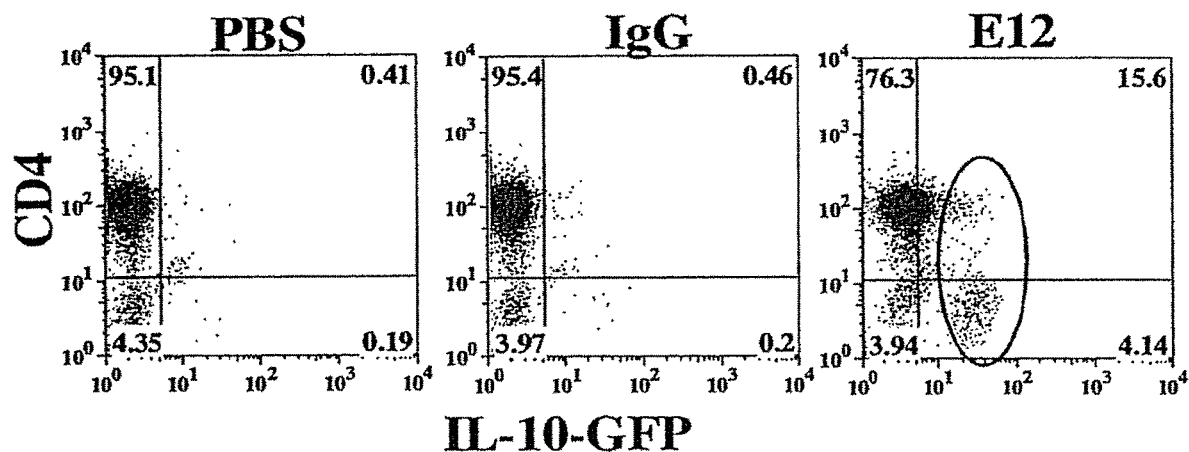
Figure 4C:
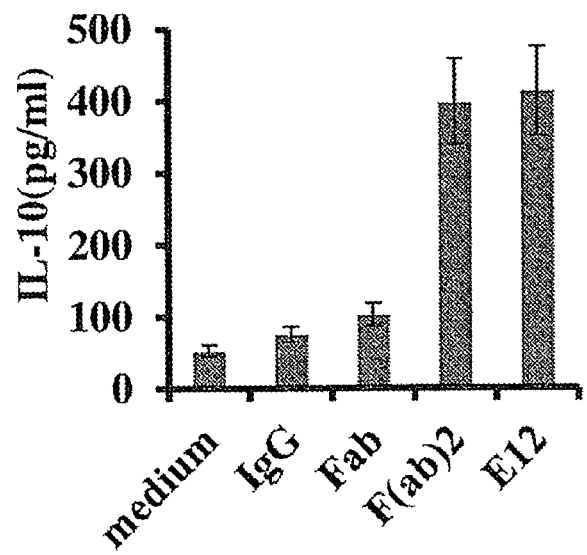
Figure 4D:
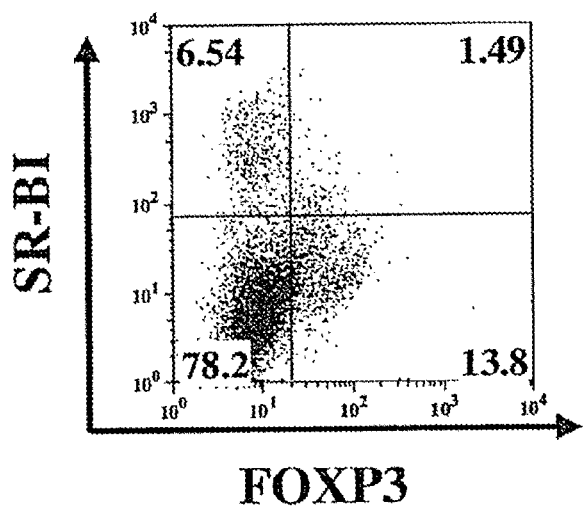
Figure 4E:
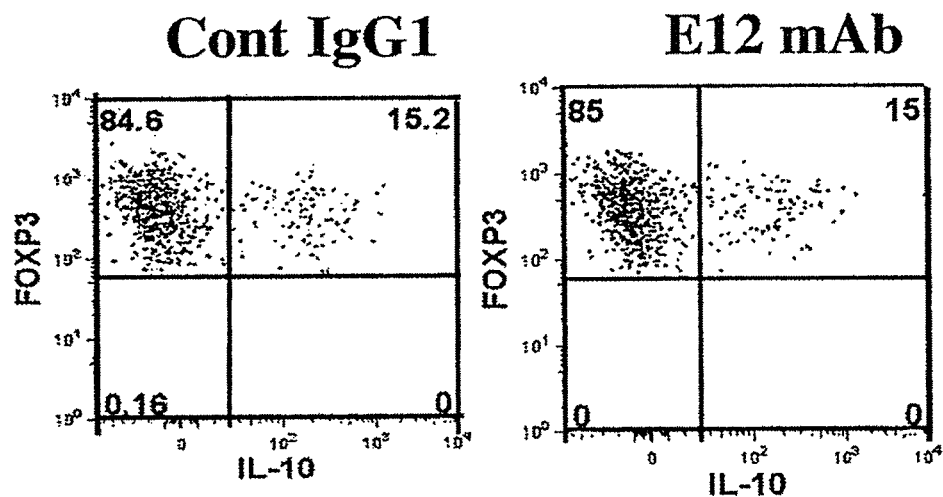
Figure 4F:
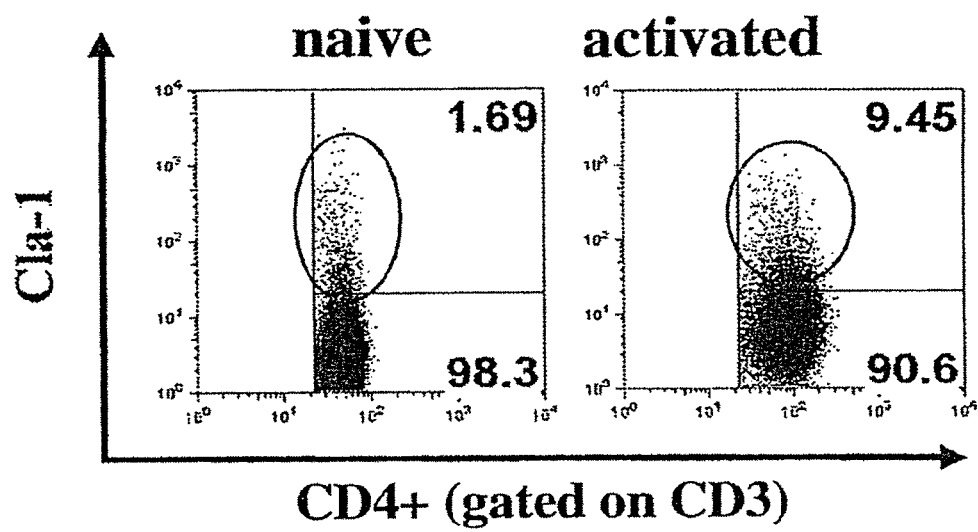
Figure 4G:
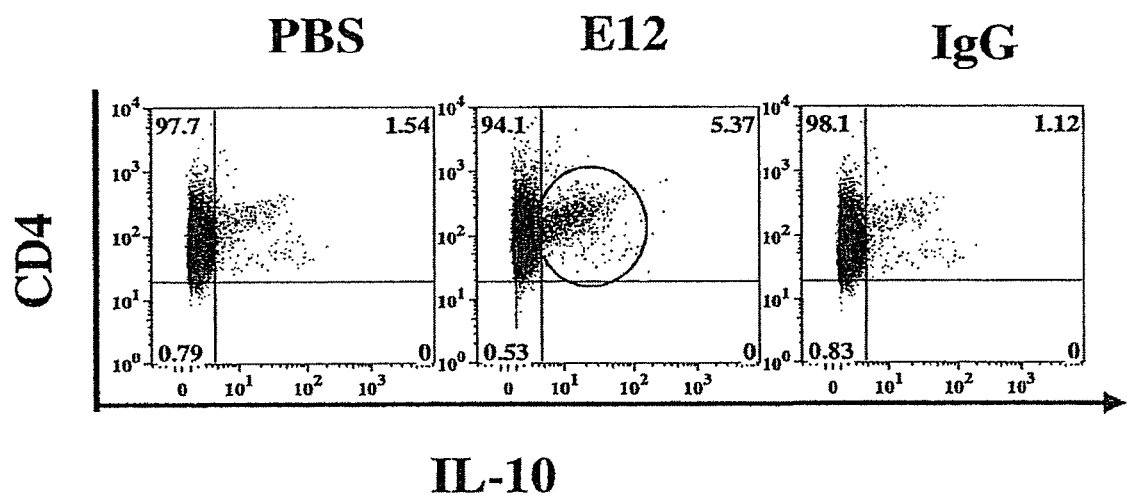

E12 mAb Drives the Polarization of FOXp3-Negative CD4+ T Cells into $IL-10^{high}$ Tr1-Like Cells Within the immune system SR-BI is known to be mostly expressed by innate immune cells (Areschoug et al. 2008, Contrib Microbiol 15, 45-60). Not much is known about its expression and direct role in CD4+ T cells. FIG. 4A shows that a small portion of naïve CD4+ T cells do express SR-BI (about 1% of CD4+ T cells isolated from the spleens of mice). Similar expression was detected in CD4+ T cells from peripheral blood (not shown). Within 24h of in vitro activation the relative number of SR-BI+CD4+ T cells was increased to about 10% of total CD4+ cells (FIG. 4A). At this time, cultures were supplemented with E12 mAb or control IgG and after 72 h the percentage of $CD4+IL10^{high}$ T cells was determined. FIG. 4B shows that in the presence of E12 mAb the relative number of $CD4+IL10^{high}$ T cells increased from 0.46% to 15.6%. To determine whether the E12 mAb acts as an agonist of its target receptor in T cells, similar to its action in macrophages, E12 mAbs were enzymatically cleaved into either single F(ab) or F(ab')$_2$ and each fragment was analyzed for its ability to induce IL-10 in CD4+ T cells. FIG. 4C shows that the native mAb as well as its F(ab')$_2$ fragment, but not the single chain F(ab), induced IL-10 in these cells, similarly to their effect in macrophages. Finally, the expression of SR-BI on FOXp3+ and FOXp3- T cells undergoing anti CD3&CD28 activation was analyzed. FIG. 4D shows that SR-BI is expressed on both T cell subsets at a similar relative ratio (about 8-10% of total number of cells in each category). Their total number are about 4-fold higher in Foxp3- CD4+ T cells (1.49 Vs 6.54%) due to their relative higher number. Hence, in contrast to FOXp3- CD4+ T cells, E12 mAb did not led to increased relative number of $FOXp3+IL-10^{high}CD4+$ T cells (FIG. 4E, 15% in Foxp3+ T cells activated in the presence or absence of E12 mAb). Collectively, the results show that by binding to its target receptor E12mAb induces CD4+ $IL-10^{high}$Foxop3- T cells. The relevance of these findings were then explored in human CD4+ T cells. The expression of CLA-1 in peripheral blood T cells from healthy donors was monitored, before and during anti CD3&CD28 induced activation Similarly to mice (see FIG. 4A) the relative number of CD4+ T cells expressing CLA-1 in non-activated T cells is low (1.69%) and it increases within 24h of activation to 9.45% (FIG. 4F). At this time cultures were supplemented with E12mAb or control IgG1 (10 ng/ml) and after an additional 48 h, IL-10 producing CD4 T cells were quantified by flow cytometry. FIG. 4 G shows that the E12 mAb skewed CD4+ T cells into $CD4+IL10^{high}$ T cells, similar to the effect on mice CD4+ T cells (FIG. 4B).

Figure 4H:
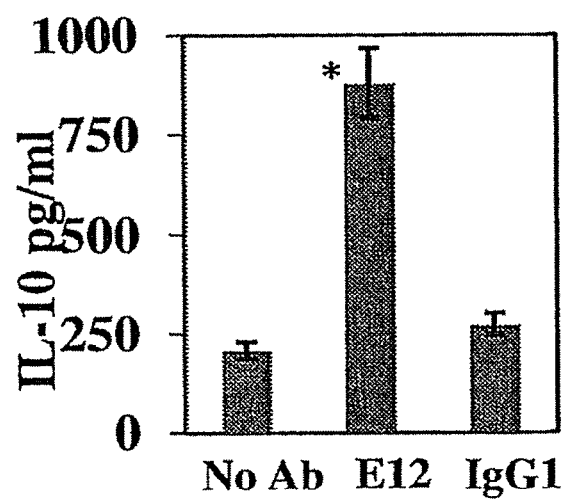

Consistently, the level of IL-10 in the supernatant was also increased in the presence of E12 mAb (FIG. 4H).

Example 6

Figure 5A:
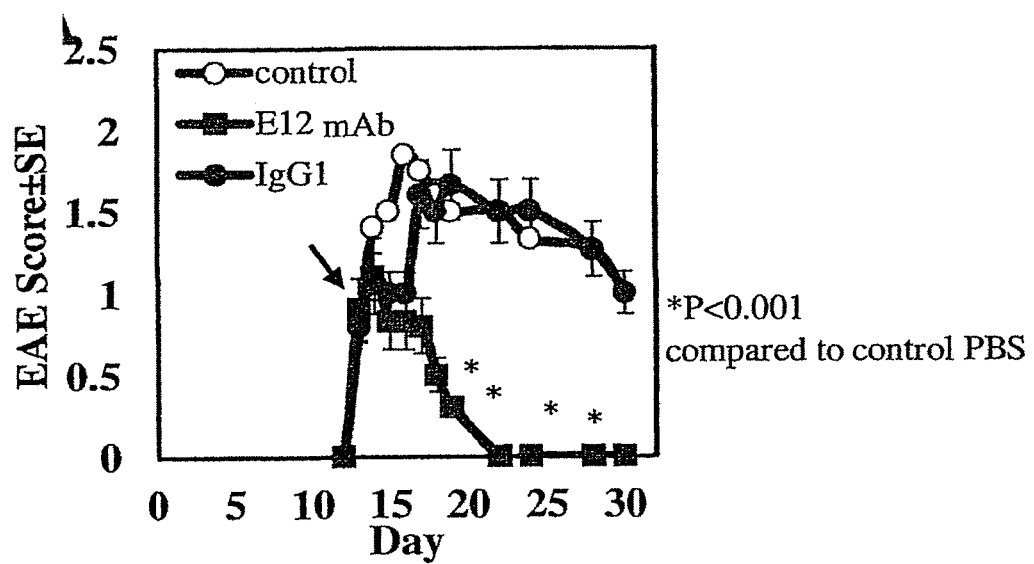
Figure 5B:
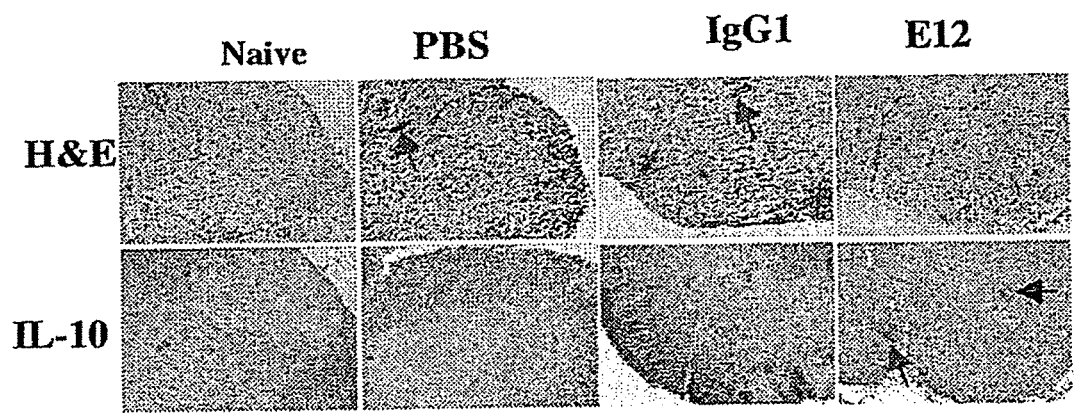
Figure 5C:
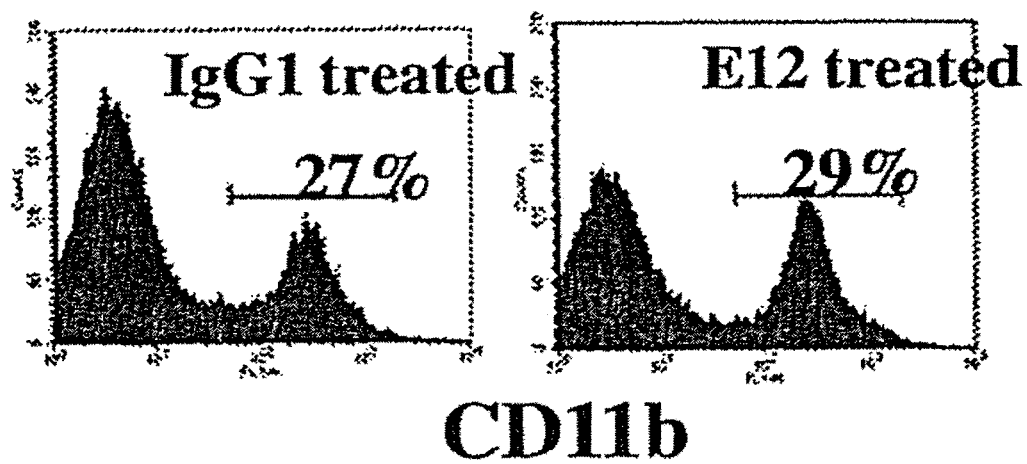
Figure 5D:
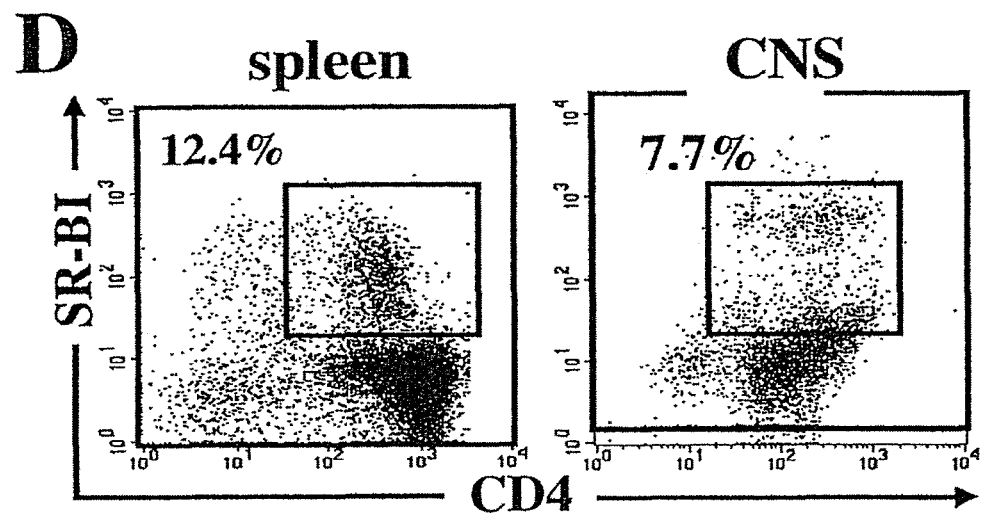

Administration of E12 mAb Suppresses Ongoing EAE and Provides a Long-Lasting State of Disease Resistance The effect of E12 mAb administration during ongoing EAE on the development and progression of the disease was examined FIG. 5A shows that repeated administration of E12 mAb (300 µg/mouse, days 11, 13 and 15) rapidly suppressed an ongoing disease. On day 18, at the peak of disease in control mice, representative mice from each group were sacrificed for analysis of different parameters associated with the progression of disease. Lumbar spinal cord sections were subjected to histological and immunohistochemical analyses. FIG. 5B shows reduced infiltration of mononuclear cells around high endothelium venules (HEV) and an increased number of IL-10 producing cells in E12 mAb treated mice. To examine the possibility that disease inhibition might result, in part, from macrophage depletion due to potential antibody dependent cell cytotoxicity (ADCC), total number of $CD11b^+$ macrophages was analyzed (flow cytometry) in spleens of mice. No difference in $CD11b^+$ macrophage number was observed between E12 mAb-treated and control mice (FIG. 5C). The level of SR-BI+ CD4+ T cells in the periphery and within the inflamed CNS during the course of EAE was also assessed. FIG. 5D shows that the level of SR-BI+ CD4+ T cells in the spleen was increased to 12.4% during EAE, in comparison to 1% in naïve mice (see FIG. 4A). In addition, CD4+ T cells were found to accumulate within the CNS (7.7% of total CD4+ T cells). Thus, during EAE, both the level of protective SR-BI autoantibodies (FIG. 1) as well as their receptor on target CD4+ T cells are increased.

Figure 5E:
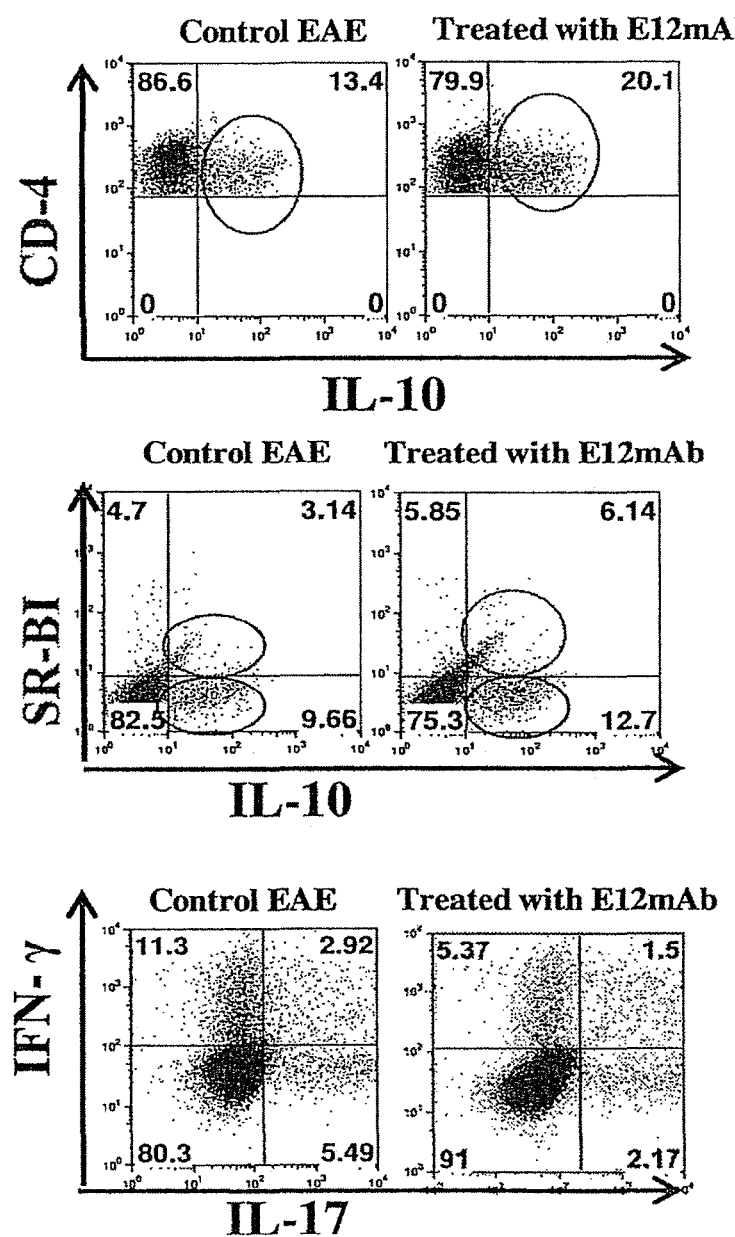
Figure 5F:
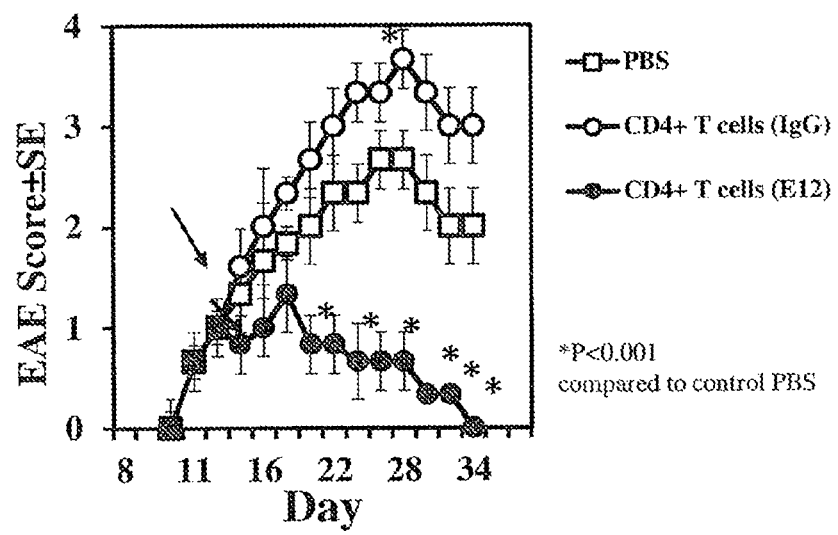
Figure 5G:
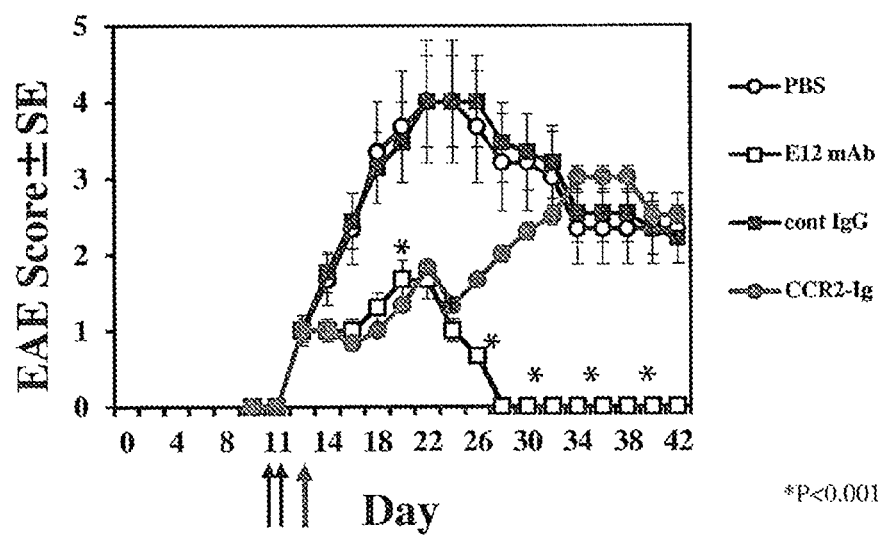

A comparative analysis of CD4+ T cell subsets within the CNS of control and E12 mAb-treated EAE mice was performed. FIG. 5E shows an increased level of $CD4+IL-10^{high}$ (from 13.4% to 20.2%). Further analysis showed an induction of IL-10 in both $SR-BI^+$ $CD4^+$ T cells (from 3.14% to 6.14%) and $SR-BI^-$ $CD4^+$ T cells (from 9.66% to 12.7%). This may be due to infectious spread of IL-10 production from SR-BI+ to SR-BI− CD4+ T cells, or receptor internalization following E12 mAb binding. IL-10 induction in CD4+ T cells was accompanied by a significant reduction in both types of effector T cells, namely $IFN-\gamma^{high}IL17^{low}$ Th1 (from 11.3% to 5.37%), $IL-17^{high}IFN-\gamma^{low}$ Th17 (from 5.49% to 2.17%) and $IL-17^{high}IFN-\gamma^{high}$ (from 2.92% to 1.5%). IL-4 producing CD4+ T cells were about 1% in all samples (not shown). Similar observations were obtained when analyzing the same parameters in CD4+ T cells isolated from the spleen (not shown). Thus, to further study the mechanistic basis of E12mAb induced disease suppression an adoptive transfer experiment was conducted in which CD4+ T cells isolated from the spleen of control or E12 mAb-treated EAE mice were activated in the presence of their target antigen (MOGp33-55) and transferred (30× $10^6$/mouse) to EAE recipient mice, at the onset of disease. While the administration of CD4+ T cells from EAE mice treated with control IgG1 aggravated its manifestation, T cells from E12 mAb treated mice led to rapid remission (FIG. 5F). These results further support the hypothesis that E12 mAb selects IL-10 producing regulatory T cells that suppress the disease. Therapies that suppress the inflammatory response directly, such as steroids and antagonists of inflammatory mediators or adhesion molecules, provide a short term effect that is dependent on continuous administration of the drug (Miller et al. 2003, The New England journal of medicine 348, 15-23). In contrast, it is conceivable that therapy aimed at potentiating T-regs may provide a longer lasting effect. To examine this possibility the long-term effect of E12 mAb and CCR2-Ig therapies administered according to a short-term protocol were compared. The latter therapy selectively targets CCL2 and by so doing the accumulation of macrophages at the site of inflammation resulting in rapid suppression of ongoing EAE (Izhak et al. 2009, Journal of immunology 183, 732-739). Mice were subjected to short-term therapy (3 repeated administrations beginning at the onset of disease, every other day, 300µg/ml E12 mAb, or control IgG1 or CCR2-Ig, or PBS), and monitored for the development and progression of disease. The administration of either E12mAb or CCR2-Ig led to rapid suppression of ongoing EAE (FIG. 5G, day 22). However, the effect of CCR2-Ig based therapy was short-lived and within 20 days after therapy was terminated mice developed full-blown disease to a similar extent as control untreated EAE mice. In contrast, E12mAb-treated mice remained in disease remission throughout the whole period of the experiment (FIG. 5G, 42 days).

Example 7

E12 mAb Selects CD4+ T Cells that Suppress EAE in an IL-10 Dependent Manner

Figure 6A:
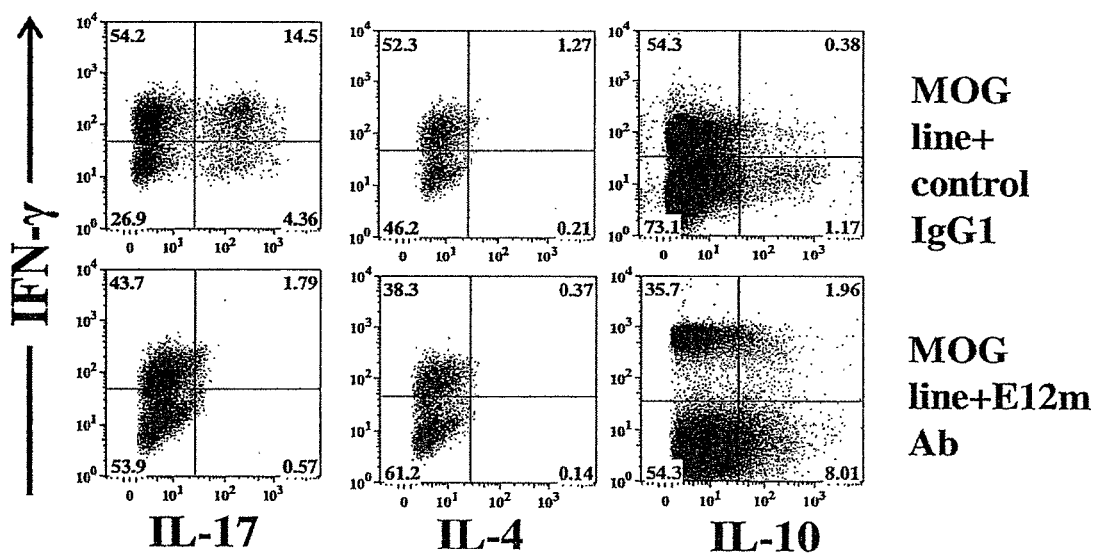
Figure 6B:
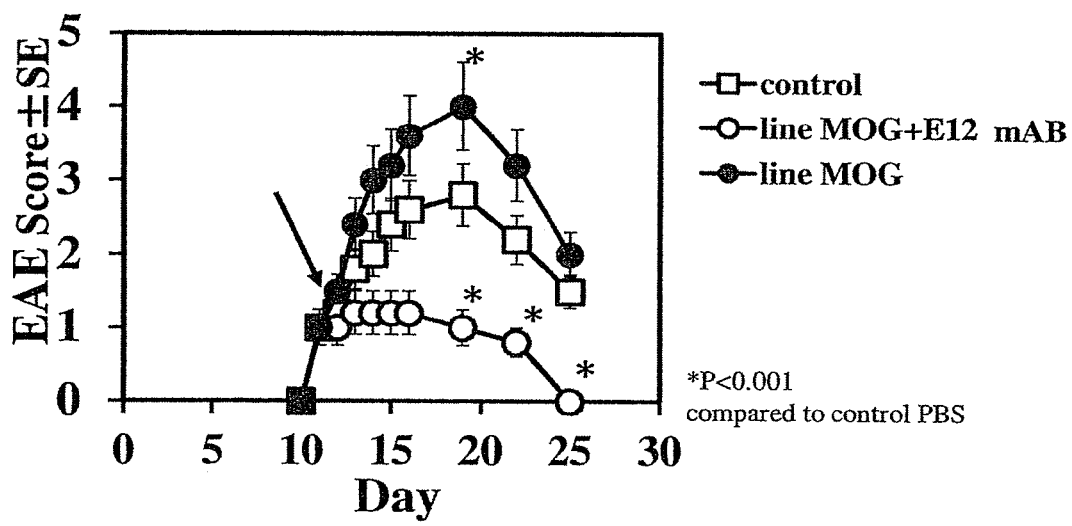
Figure 6C:
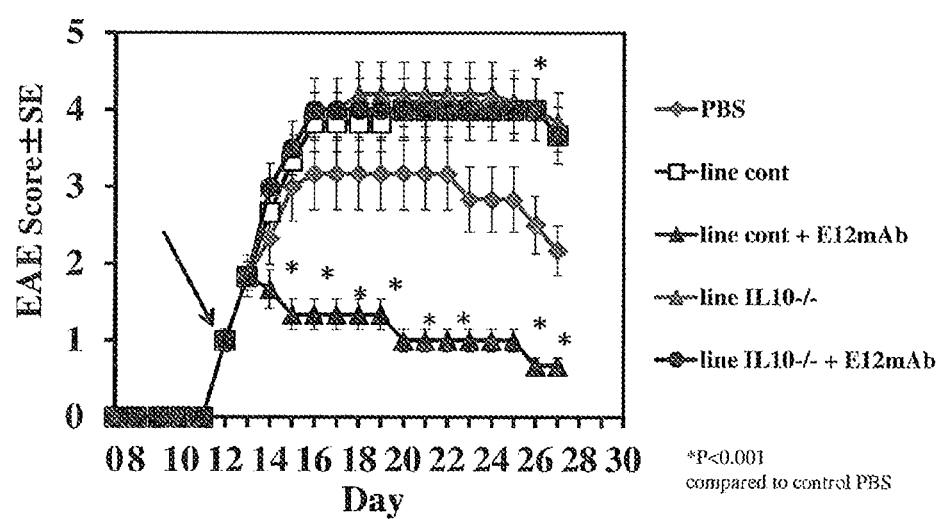

To test the hypothesis that E12mAb also directs the polarization of MOG specific CD4+ T cells during in vitro stimulation MOGp33-55 specific CD4+ encephalitogenic T cell line was selected from primary lymph nodes (Wildbaum et al. 2010, The American journal of pathology 176, 2764-2775). During the second stimulation cycle cultures were supplemented with 10 µg/ml E12mAb, control IgG1, or PBS. After 72 h, cells were harvestedand their cytokine profile was analyzed by flow cytometry (FIG. 6A shows that activation of the MOGp33-55 specific T cell line in the presence of E12mAb resulted in a marked reduction in $IL17^{high}$ producing CD4+ T cells (from 18.86% to 2.36%) that includes both $IL-17^{high}IFN-\gamma^{high}$ (from 14.5% to 1.79%) and $IL-17^{high}IFN-\gamma^{low}$ (from 4.36% to 0.57%), a reduction in $IFN-\gamma^{high}$ $IL-17^{low}$ Th1 cells (from 54.2 to 43.7%) and a marked elevation in $IL-10^{high}$ producing T cells (from 1.55% to 9.18%). No difference was observed when cultures were supplemented with control IgG1 (10 µg/ml) or PBS. The ability of these cells to suppress ongoing MOGp33-55-induced EAE was tested in an adoptive transfer experiment. The harvested cells were transferred to mice developing active EAE at the onset of disease (20×$10^6$ cells/mouse). FIG. 6B shows that while mice injected with the effector line co-cultured with control IgG1 displayed an aggravated form of disease, those injected with the line cultured in the presence of E12mAb exhibited a significantly lower manifestation of EAE. To test the role of IL-10 in the E12 mAb-mediated suppressive effect, the same setup of transferred disease was used, but donor mice were either WT or IL10 deficient. As expected, administration of CD4+ T cells from WT mice that were co-cultured with E12mAb suppressed ongoing EAE. In contrast, administration of CD4+ T cells from IL-10−/− mice, cultured in the presence or absence of E12 mAb, aggravated the disease, as did the CD4+ T cell line from WT mice cultured in the absence of E12 mAb (FIG. 6C). Collectively the results demonstrate that antibody binding to the 11-amino acid epitope of SR-BI on the surface of Tr1-like CD4+ T cells has a significant role in the regulation of EAE in an IL-10 dependent manner.

What is claimed is:

1. A peptide consisting of the amino acid sequence set forth in EFYSPEACRSM (SEQ ID NO: 1) or EFFSPEACRSM (SEQ ID NO: 2), wherein the peptide is: (1) attached to a detectable label; (2) attached to a detectable tag selected from the group consisting of: chitin binding protein (CBP)-tag, maltose binding protein (MBP)-tag, glutathione-S-transferase (GST)-tag, poly-histidine tag, FLAG tag, an epitope tag, or a fluorescence tag; (3) connected to a solid support selected from the group consisting of: cross-linked dextran, polyvinyl chlorite, an assay plate, a test tube, a particulate material, a bead, a colloidal metal, a porous matrix, and an iron oxide particle, or (4) cross-linked to a solid-phase substrate via a cross-linking agent.

2. The peptide of claim 1, wherein said poly-histidine tag comprises a 6XHis tag.

3. The peptide of claim 1, wherein said epitope tag comprises a V5-tag, c-myc-tag, or a Hemagglutinin (HA)-tag.

4. The peptide of claim 1, wherein said fluorescence tag comprises green fluorescent protein (GFP), red fluorescent protein (RFP), yellow fluorescent protein (YIP), blue fluorescent protein (BFP), or cyan fluorescent protein (CFP).

5. The peptide of claim 1, wherein said solid support is a porous matrix, a polymeric bead, a colloidal metal, or an iron oxide particle.

6. The peptide of claim 1, wherein amino acids of said peptide are L or D stereoisomers or a combination thereof.

7. The peptide of claim 1, wherein said particulate material comprises filter paper, agarose, cross-linked dextran, or other polysaccharides.

8. The peptide of claim 1, wherein said bead is a plastic bead, a glass bead, or a paramagnetic bead.

9. The peptide of claim 1, wherein said colloidal metal comprises a colloidal gold particle or a colloidal silver particle.

10. The peptide of to claim 1, wherein said assay plate or test tube is manufactured from polyethylene, polypropylene, or polystyrene.

11. The peptide of claim 1, wherein said assay plate comprises a microtiter plate.

* * * * *

SEQUENCE LISTING

<160> NUMBER OF SEQ ID NOS: 38

<210> SEQ ID NO 1
<211> LENGTH: 11
<212> TYPE: PRT
<213> ORGANISM: Homo sapiens

<400> SEQUENCE: 1

Glu Phe Tyr Ser Pro Glu Ala Cys Arg Ser Met
1               5                   10

<210> SEQ ID NO 2
<211> LENGTH: 11
<212> TYPE: PRT
<213> ORGANISM: Homo sapiens

<400> SEQUENCE: 2

Glu Phe Phe Ser Pro Glu Ala Cys Arg Ser Met
1               5                   10

<210> SEQ ID NO 3
<211> LENGTH: 509
<212> TYPE: PRT
<213> ORGANISM: Homo sapiens

<400> SEQUENCE: 3

Met Gly Gly Ser Ser Arg Ala Arg Trp Val Ala Leu Gly Leu Gly Ala
1               5                   10                  15

Leu Gly Leu Leu Phe Ala Ala Leu Gly Val Val Met Ile Leu Met Val
                20                  25                  30

Pro Ser Leu Ile Lys Gln Gln Val Leu Lys Asn Val Arg Ile Asp Pro
                35                  40                  45

Ser Ser Leu Ser Phe Gly Met Trp Lys Glu Ile Pro Val Pro Phe Tyr
        50                  55                  60

Leu Ser Val Tyr Phe Phe Glu Val Val Asn Pro Asn Glu Val Leu Asn
65                  70                  75                  80

Gly Gln Lys Pro Val Val Arg Glu Arg Gly Pro Tyr Val Tyr Arg Glu
                85                  90                  95

Phe Arg Gln Lys Val Asn Ile Thr Phe Asn Asp Asn Asp Thr Val Ser
                100                 105                 110

Phe Val Glu Asn Arg Ser Leu His Phe Gln Pro Asp Lys Ser His Gly
                115                 120                 125

Ser Glu Ser Asp Tyr Ile Val Leu Pro Asn Ile Leu Val Leu Gly Gly
        130                 135                 140

Ser Ile Leu Met Glu Ser Lys Pro Val Ser Leu Lys Leu Met Met Thr
145                 150                 155                 160

Leu Ala Leu Val Thr Met Gly Gln Arg Ala Phe Met Asn Arg Thr Val
                165                 170                 175

Gly Glu Ile Leu Trp Gly Tyr Asp Asp Pro Phe Val His Phe Leu Asn
                180                 185                 190

Thr Tyr Leu Pro Asp Met Leu Pro Ile Lys Gly Lys Phe Gly Leu Phe
                195                 200                 205

Val Gly Met Asn Asn Ser Asn Ser Gly Val Phe Thr Val Phe Thr Gly
        210                 215                 220

Val Gln Asn Phe Ser Arg Ile His Leu Val Asp Lys Trp Asn Gly Leu
225                 230                 235                 240

-continued

Ser Lys Ile Asp Tyr Trp His Ser Glu Gln Cys Asn Met Ile Asn Gly
            245                 250                 255

Thr Ser Gly Gln Met Trp Ala Pro Phe Met Thr Pro Glu Ser Ser Leu
        260                 265                 270

Glu Phe Phe Ser Pro Glu Ala Cys Arg Ser Met Lys Leu Thr Tyr Asn
    275                 280                 285

Glu Ser Arg Val Phe Glu Gly Ile Pro Thr Tyr Arg Phe Thr Ala Pro
290                 295                 300

Asp Thr Leu Phe Ala Asn Gly Ser Val Tyr Pro Pro Asn Glu Gly Phe
305                 310                 315                 320

Cys Pro Cys Arg Glu Ser Gly Ile Gln Asn Val Ser Thr Cys Arg Phe
                325                 330                 335

Gly Ala Pro Leu Phe Leu Ser His Pro His Phe Tyr Asn Ala Asp Pro
            340                 345                 350

Val Leu Ser Glu Ala Val Leu Gly Leu Asn Pro Asn Pro Lys Glu His
        355                 360                 365

Ser Leu Phe Leu Asp Ile His Pro Val Thr Gly Ile Pro Met Asn Cys
    370                 375                 380

Ser Val Lys Met Gln Leu Ser Leu Tyr Ile Lys Ser Val Lys Gly Ile
385                 390                 395                 400

Gly Gln Thr Gly Lys Ile Glu Pro Val Leu Pro Leu Leu Trp Phe
                405                 410                 415

Glu Gln Ser Gly Ala Met Gly Gly Lys Pro Leu Ser Thr Phe Tyr Thr
            420                 425                 430

Gln Leu Val Leu Met Pro Gln Val Leu His Tyr Ala Gln Tyr Val Leu
        435                 440                 445

Leu Gly Leu Gly Leu Leu Leu Leu Val Pro Ile Ile Cys Gln Leu
    450                 455                 460

Arg Ser Gln Glu Lys Cys Phe Leu Phe Trp Ser Gly Ser Lys Lys Gly
465                 470                 475                 480

Ser Gln Asp Lys Glu Ala Ile Gln Ala Tyr Ser Glu Ser Leu Met Ser
                485                 490                 495

Pro Ala Ala Lys Gly Thr Val Leu Gln Glu Ala Lys Leu
            500                 505

<210> SEQ ID NO 4
<211> LENGTH: 509
<212> TYPE: PRT
<213> ORGANISM: Homo sapiens

<400> SEQUENCE: 4

Met Gly Cys Ser Ala Lys Ala Arg Trp Ala Gly Ala Leu Gly Val
1               5                   10                  15

Ala Gly Leu Leu Cys Ala Val Leu Gly Ala Val Met Ile Val Met Val
            20                  25                  30

Pro Ser Leu Ile Lys Gln Gln Val Leu Lys Asn Val Arg Ile Asp Pro
        35                  40                  45

Ser Ser Leu Ser Phe Asn Met Trp Lys Glu Ile Pro Ile Pro Phe Tyr
    50                  55                  60

Leu Ser Val Tyr Phe Phe Asp Val Met Asn Pro Ser Glu Ile Leu Lys
65                  70                  75                  80

Gly Glu Lys Pro Gln Val Arg Glu Arg Gly Pro Tyr Val Tyr Arg Glu
                85                  90                  95

Ser Arg His Lys Ser Asn Ile Thr Phe Asn Asn Asn Asp Thr Val Ser

```
            100                 105                 110
Phe Leu Glu Tyr Arg Thr Phe Gln Phe Gln Pro Ser Lys Ser His Gly
        115                 120                 125

Ser Glu Ser Asp Tyr Ile Val Met Pro Asn Ile Leu Val Leu Gly Ala
    130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
            180                 185                 190

Lys Tyr Phe Pro Gly Met Phe Pro Phe Lys Asp Lys Phe Gly Leu Phe
        195                 200                 205

Ala Glu Leu Asn Asn Ser Asp Ser Gly Leu Phe Thr Val Phe Thr Gly
    210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255

Thr Ser Gly Gln Met Trp Pro Pro Phe Met Thr Pro Glu Ser Ser Leu
            260                 265                 270

Glu Phe Tyr Ser Pro Glu Ala Cys Arg Ser Met Lys Leu Met Tyr Lys
        275                 280                 285

Glu Ser Gly Val Phe Glu Gly Ile Pro Thr Tyr Arg Phe Val Ala Pro
    290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Ser Ala Pro Leu Phe Leu Ser His Pro His Phe Leu Asn Ala Asp Pro
            340                 345                 350

Val Leu Ala Glu Ala Val Thr Gly Leu His Pro Asn Gln Glu Ala His
        355                 360                 365

Ser Leu Phe Leu Asp Ile His Pro Val Thr Gly Ile Pro Met Asn Cys
    370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Val Leu Pro Leu Leu Trp Phe
                405                 410                 415

Ala Glu Ser Gly Ala Met Glu Gly Glu Thr Leu His Thr Phe Tyr Thr
            420                 425                 430

Gln Leu Val Leu Met Pro Lys Val Met His Tyr Ala Gln Tyr Val Leu
        435                 440                 445

Leu Ala Leu Gly Cys Val Leu Leu Val Pro Val Ile Cys Gln Ile
    450                 455                 460

Arg Ser Gln Glu Lys Cys Tyr Leu Phe Trp Ser Ser Lys Lys Gly
465                 470                 475                 480

Ser Lys Asp Lys Glu Ala Ile Gln Ala Tyr Ser Glu Ser Leu Met Thr
                485                 490                 495

Ser Ala Pro Lys Gly Ser Val Leu Gln Glu Ala Lys Leu
            500                 505

<210> SEQ ID NO 5
```

-continued

```
<211> LENGTH: 40
<212> TYPE: DNA
<213> ORGANISM: Artificial Sequence
<220> FEATURE:
<223> OTHER INFORMATION: Primer

<400> SEQUENCE: 5
ggaattccat atggagatga acgtgcgcat cgaccccagt                    40

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
cccaagcttc tgagtgtaga atgtgtgaag a                             31

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
gctgatatcg ccccaccaga gccctgcgag                               30

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
cccaagcttt caagctccgg cggtgactac                               30

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
cccaagctta tggagcgtgt gcttggcttg                               30

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
cgcggatcct taaacaaaga ggcgatctcc                               30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
```
gctgacactt gggaaatgaa gaactgctta                    30

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
cccaagcttt catgaagtac aagtgacccc                    30

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
gctgacactt gggaaatgaa gaactgctta                    30

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
cccaagcttt catgaagtac aagtgacccc                    30

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
gctgatatcg gagacatgct tattgagaag                    30

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
cccaagcttt cacacaggct ttccttcttt                    30

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
gctgatatca tccatctggt ggataagtg                     29

<210> SEQ ID NO 18
<211> LENGTH: 29
<212> TYPE: DNA

<213> ORGANISM: Artificial Sequence
<220> FEATURE:
<223> OTHER INFORMATION: Primer

<400> SEQUENCE: 18
cccaagcttt cagatcccag tgaccgggt                                       29

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
cccaagctta tgggctgtga tcggaactgt                                      30

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
cgcggatcct tattttccat tcttggattt                                      30

<210> SEQ ID NO 21
<211> LENGTH: 31
<212> TYPE: DNA
<213> ORGANISM: Artificial Sequence
<220> FEATURE:
<223> OTHER INFORMATION: Primer

<400> SEQUENCE: 21
cccaagctta tggaagacaa taatatgtta c                                    31

<210> SEQ ID NO 22
<211> LENGTH: 31
<212> TYPE: DNA
<213> ORGANISM: Artificial Sequence
<220> FEATURE:
<223> OTHER INFORMATION: Primer

<400> SEQUENCE: 22
ccgctcgagc acactggttt tatgacaagg c                                    31

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
cccaagctta gatctcagaa agaaggttt                                       29

<210> SEQ ID NO 24
<211> LENGTH: 29
<212> TYPE: DNA
<213> ORGANISM: Artificial Sequence
<220> FEATURE:
<223> OTHER INFORMATION: Primer

<400> SEQUENCE: 24
ccgctcgagc tttaatgttt ggaaactct                                       29

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
gctgatatct ttaaaatcga gatctcccc                                29

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
ccggaattct caagagtgct catcctcaa                                29

<210> SEQ ID NO 27
<211> LENGTH: 64
<212> TYPE: PRT
<213> ORGANISM: Artificial Sequence
<220> FEATURE:
<223> OTHER INFORMATION: Synthetic peptide

<400> SEQUENCE: 27

Ile His Leu Val Asp Lys Trp Asn Gly Leu Ser Glu Val Lys Tyr Trp
1               5                   10                  15

His Ser Glu Gln Cys Asn Met Ile Asn Gly Thr Ala Gly Gln Met Trp
            20                  25                  30

Ala Pro Phe Met Thr Pro Glu Ser Ser Leu Glu Phe Phe Ser Pro Glu
        35                  40                  45

Ala Cys Arg Ser Met Lys Leu Thr Tyr Gln Ser Gly Val Phe Glu
    50                  55                  60

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide

<400> SEQUENCE: 28

Ile His Leu Val Asp Lys Trp Asn Gly Leu Ser
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic peptide

<400> SEQUENCE: 29

Val Asp Lys Trp Asn Gly Leu Ser Glu Val
1               5                   10

<210> SEQ ID NO 30
<211> LENGTH: 11
<212> TYPE: PRT
<213> ORGANISM: Artificial Sequence
<220> FEATURE:

<223> OTHER INFORMATION: Synthetic peptide

<400> SEQUENCE: 30

Ser Glu Val Lys Tyr Trp His Ser Glu Gln Cys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic peptide

<400> SEQUENCE: 31

Glu Gln Cys Asn Met Ile Asn Gly Thr Ala Gly
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide

<400> SEQUENCE: 32

Thr Ala Gly Gln Met Trp Ala Pro Phe Met Thr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic peptide

<400> SEQUENCE: 33

Phe Met Thr Pro Glu Ser Ser Leu Glu Phe Phe
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic peptide

<400> SEQUENCE: 34

Glu Phe Phe Ser Pro Glu Ala Cys Arg Ser Met
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic peptide

<400> SEQUENCE: 35

Arg Ser Met Lys Leu Thr Tyr Gln Glu Ser
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 36

Gln Glu Ser Gly Val Phe Glu
1               5

<210> SEQ ID NO 37
<211> LENGTH: 64
<212> TYPE: PRT
<213> ORGANISM: Homo sapiens

<400> SEQUENCE: 37

Ile His Leu Val Asp Lys Trp Asn Gly Leu Ser Glu Val Lys Tyr Trp
1               5                   10                  15

His Ser Glu Gln Cys Asn Met Ile Asn Gly Thr Ala Gly Gln Met Trp
                20                  25                  30

Ala Pro Phe Met Thr Pro Glu Ser Ser Leu Glu Phe Phe Ser Pro Glu
            35                  40                  45

Ala Cys Arg Ser Met Lys Leu Thr Tyr Gln Glu Ser Arg Val Phe Glu
        50                  55                  60

<210> SEQ ID NO 38
<211> LENGTH: 64
<212> TYPE: PRT
<213> ORGANISM: Homo sapiens

<400> SEQUENCE: 38

Ile His Leu Val Asp Lys Trp Asn Gly Leu Ser Lys Val Asp Phe Trp
1               5                   10                  15

His Ser Asp Gln Cys Asn Met Ile Asn Gly Thr Ser Gly Gln Met Trp
                20                  25                  30

Pro Pro Phe Met Thr Pro Glu Ser Ser Leu Glu Phe Tyr Ser Pro Glu
            35                  40                  45

Ala Cys Arg Ser Met Lys Leu Met Tyr Lys Glu Ser Gly Val Phe Glu
        50                  55                  60
```